United States Patent
Ling

(10) Patent No.: US 9,884,918 B2
(45) Date of Patent: *Feb. 6, 2018

(54) HER2DELTA16 PEPTIDES

(71) Applicant: NESTEC S.A., Vevey (CH)

(72) Inventor: Nicholas Chi-Kwan Ling, San Diego, CA (US)

(73) Assignee: Nestec S.A., Vevey (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/465,508

(22) Filed: Mar. 21, 2017

(65) Prior Publication Data

US 2017/0298144 A1    Oct. 19, 2017

Related U.S. Application Data

(63) Continuation of application No. 14/712,165, filed on May 14, 2015, now Pat. No. 9,630,993, which is a continuation of application No. 13/901,210, filed on May 23, 2013, now Pat. No. 9,062,096, which is a continuation of application No. PCT/US2011/062954, filed on Dec. 1, 2011.

(60) Provisional application No. 61/419,210, filed on Dec. 2, 2010.

(51) Int. Cl.
| | |
|---|---|
| *C07K 7/64* | (2006.01) |
| *A61K 38/00* | (2006.01) |
| *C07K 16/32* | (2006.01) |
| *A61K 47/48* | (2006.01) |
| *C07K 14/82* | (2006.01) |
| *G01N 33/574* | (2006.01) |

(52) U.S. Cl.
CPC ........ *C07K 16/32* (2013.01); *A61K 47/48569* (2013.01); *C07K 14/82* (2013.01); *G01N 33/57415* (2013.01); *C07K 2317/24* (2013.01)

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. | |
| 7,737,253 B2 | 6/2010 | Robins et al. | |
| 9,062,096 B2 | 6/2015 | Ling | |
| 9,630,993 B2 | 4/2017 | Ling | |
| 2006/0177448 A1* | 8/2006 | Carey ................ | C07K 16/30 424/146.1 |
| 2013/0317195 A1 | 11/2013 | Ling | |
| 2015/0315291 A1 | 11/2015 | Ling | |

FOREIGN PATENT DOCUMENTS

| | | |
|---|---|---|
| WO | 2000/020579 A1 | 4/2000 |
| WO | 2002/081649 A2 | 10/2002 |
| WO | 2003/087338 A2 | 10/2003 |
| WO | 2005/007198 A2 | 1/2005 |

OTHER PUBLICATIONS

Mitra, D. et al., "An oncogenic isoform of HER2 associated with locally disseminated breast cancer and trastuzumab resistance," Molecular Cancer Therapeutics, Aug. 2009, vol. 8, No. 8, pp. 2152-2162.

Park et al., "Rationally designed anti-HER2/neu peptide mimetic disables P185HER2/neu tyrosine kinases in vitro and in vivo," Nature Biotechnology, Feb. 2000, vol. 18, pp. 194-198.

\* cited by examiner

*Primary Examiner* — Jeanette Lieb
(74) *Attorney, Agent, or Firm* — Kilpatrick Townsend and Stockton LLP

(57) ABSTRACT

The present invention provides cyclic peptides comprising a dimer of peptides, each peptide comprising a sequence corresponding to the HER2 splice variant HER2Delta16, wherein the cyclic peptide is cyclized via a disulfide bond between the peptides and via an amino acid linking the peptides. The invention also provides methods of making antibodies that specifically bind to HER2Delta16 homodimers using said cyclic peptides.

20 Claims, 5 Drawing Sheets

MPA-Pro-Ile-Asn-Cys-Thr-His-Ser-Cys-Val-Asp-Leu-Asp-Asp-Lys-Gly-Cys-Pro-Ala-Glu-Gln-Arg-Ala-Ser-Pro-Le

SEQUENCE LISTING

```
<160> NUMBER OF SEQ ID NOS: 245

<210> SEQ ID NO 1
<211> LENGTH: 10
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers

<400> SEQUENCE: 1

Pro Ile Asn Cys Thr His Ser Pro Leu Thr
1               5                   10

<210> SEQ ID NO 2
<211> LENGTH: 10
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 2

Pro Leu Asn Cys Thr His Ser Pro Leu Thr
1               5                   10

<210> SEQ ID NO 3
<211> LENGTH: 10
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 3

Pro Val Asn Cys Thr His Ser Pro Leu Thr
1               5                   10

<210> SEQ ID NO 4
<211> LENGTH: 10
<212> TYPE: PRT
```

```
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 4

Pro Ile Asn Met Thr His Ser Pro Leu Thr
1               5                   10

<210> SEQ ID NO 5
<211> LENGTH: 10
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 5

Pro Ile Asn Cys Ser His Ser Pro Leu Thr
1               5                   10

<210> SEQ ID NO 6
<211> LENGTH: 10
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 6

Pro Ile Asn Cys Thr His Thr Pro Leu Thr
1               5                   10

<210> SEQ ID NO 7
<211> LENGTH: 10
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 7

Pro Ile Asn Cys Thr His Ser Pro Ile Thr
1               5                   10

<210> SEQ ID NO 8
<211> LENGTH: 10
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 8

Pro Ile Asn Cys Thr His Ser Pro Val Thr
1               5                   10

<210> SEQ ID NO 9
<211> LENGTH: 10
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
``` peptide monomers with conservative substitutions

<400> SEQUENCE: 9

Pro Ile Asn Cys Thr His Ser Pro Leu Ser
1               5                   10

<210> SEQ ID NO 10
<211> LENGTH: 10
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 10

Pro Leu Asn Met Thr His Ser Pro Leu Thr
1               5                   10

<210> SEQ ID NO 11
<211> LENGTH: 10
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 11

Pro Val Asn Met Thr His Ser Pro Leu Thr
1               5                   10

<210> SEQ ID NO 12
<211> LENGTH: 10
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 12

Pro Leu Asn Cys Ser His Ser Pro Leu Thr
1               5                   10

<210> SEQ ID NO 13
<211> LENGTH: 10
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 13

Pro Val Asn Cys Ser His Ser Pro Leu Thr
1               5                   10

<210> SEQ ID NO 14
<211> LENGTH: 10
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 14

Pro Leu Asn Cys Thr His Thr Pro Leu Thr
1               5                   10

<210> SEQ ID NO 15
<211> LENGTH: 10
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 15

Pro Val Asn Cys Thr His Thr Pro Leu Thr
1               5                   10

<210> SEQ ID NO 16
<211> LENGTH: 10
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 16

Pro Leu Asn Cys Thr His Ser Pro Ile Thr
1               5                   10

<210> SEQ ID NO 17
<211> LENGTH: 10
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 17

Pro Val Asn Cys Thr His Ser Pro Ile Thr
1               5                   10

<210> SEQ ID NO 18
<211> LENGTH: 10
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 18

Pro Leu Asn Cys Thr His Ser Pro Val Thr
1               5                   10

<210> SEQ ID NO 19
<211> LENGTH: 10
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 19

Pro Val Asn Cys Thr His Ser Pro Val Thr
1               5                   10

```
<210> SEQ ID NO 20
<211> LENGTH: 10
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 20

Pro Leu Asn Cys Thr His Ser Pro Leu Ser
1               5                   10

<210> SEQ ID NO 21
<211> LENGTH: 10
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 21

Pro Val Asn Cys Thr His Ser Pro Leu Ser
1               5                   10

<210> SEQ ID NO 22
<211> LENGTH: 10
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 22

Pro Ile Asn Met Ser His Ser Pro Leu Thr
1               5                   10

<210> SEQ ID NO 23
<211> LENGTH: 10
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 23

Pro Ile Asn Met Thr His Thr Pro Leu Thr
1               5                   10

<210> SEQ ID NO 24
<211> LENGTH: 10
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 24

Pro Ile Asn Met Thr His Ser Pro Ile Thr
1               5                   10

<210> SEQ ID NO 25
<211> LENGTH: 10
<212> TYPE: PRT
<213> ORGANISM: Artificial Sequence
```

```
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 25

Pro Ile Asn Met Thr His Ser Pro Val Thr
1               5                   10

<210> SEQ ID NO 26
<211> LENGTH: 10
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 26

Pro Ile Asn Met Thr His Ser Pro Leu Ser
1               5                   10

<210> SEQ ID NO 27
<211> LENGTH: 10
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 27

Pro Ile Asn Cys Ser His Thr Pro Leu Thr
1               5                   10

<210> SEQ ID NO 28
<211> LENGTH: 10
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 28

Pro Ile Asn Cys Ser His Ser Pro Ile Thr
1               5                   10

<210> SEQ ID NO 29
<211> LENGTH: 10
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 29

Pro Ile Asn Cys Ser His Ser Pro Val Thr
1               5                   10

<210> SEQ ID NO 30
<211> LENGTH: 10
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions
```

<400> SEQUENCE: 30

Pro Ile Asn Cys Ser His Ser Pro Leu Ser
1               5                   10

<210> SEQ ID NO 31
<211> LENGTH: 10
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 31

Pro Ile Asn Cys Thr His Thr Pro Ile Thr
1               5                   10

<210> SEQ ID NO 32
<211> LENGTH: 10
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 32

Pro Ile Asn Cys Thr His Thr Pro Val Thr
1               5                   10

<210> SEQ ID NO 33
<211> LENGTH: 10
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 33

Pro Ile Asn Cys Thr His Thr Pro Leu Ser
1               5                   10

<210> SEQ ID NO 34
<211> LENGTH: 10
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 34

Pro Ile Asn Cys Thr His Ser Pro Ile Ser
1               5                   10

<210> SEQ ID NO 35
<211> LENGTH: 10
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 35

Pro Ile Asn Cys Thr His Ser Pro Val Ser

<210> SEQ ID NO 36
<211> LENGTH: 10
<212> TYPE: PRT
<213> ORGANISM: Artificial Sequence
<220> FEATURE:
<223> OTHER INFORMATION: synthetic exon 16-deleted human epidermal
growth factor receptor 2 (HER2delta16) first and second
peptide monomers with conservative substitutions

<400> SEQUENCE: 36

Pro Leu Asn Met Ser His Ser Pro Leu Thr
1               5                   10

<210> SEQ ID NO 37
<211> LENGTH: 10
<212> TYPE: PRT
<213> ORGANISM: Artificial Sequence
<220> FEATURE:
<223> OTHER INFORMATION: synthetic exon 16-deleted human epidermal
growth factor receptor 2 (HER2delta16) first and second
peptide monomers with conservative substitutions

<400> SEQUENCE: 37

Pro Val Asn Met Ser His Ser Pro Leu Thr
1               5                   10

<210> SEQ ID NO 38
<211> LENGTH: 10
<212> TYPE: PRT
<213> ORGANISM: Artificial Sequence
<220> FEATURE:
<223> OTHER INFORMATION: synthetic exon 16-deleted human epidermal
growth factor receptor 2 (HER2delta16) first and second
peptide monomers with conservative substitutions

<400> SEQUENCE: 38

Pro Leu Asn Met Thr His Thr Pro Leu Thr
1               5                   10

<210> SEQ ID NO 39
<211> LENGTH: 10
<212> TYPE: PRT
<213> ORGANISM: Artificial Sequence
<220> FEATURE:
<223> OTHER INFORMATION: synthetic exon 16-deleted human epidermal
growth factor receptor 2 (HER2delta16) first and second
peptide monomers with conservative substitutions

<400> SEQUENCE: 39

Pro Val Asn Met Thr His Thr Pro Leu Thr
1               5                   10

<210> SEQ ID NO 40
<211> LENGTH: 10
<212> TYPE: PRT
<213> ORGANISM: Artificial Sequence
<220> FEATURE:
<223> OTHER INFORMATION: synthetic exon 16-deleted human epidermal
growth factor receptor 2 (HER2delta16) first and second
peptide monomers with conservative substitutions

<400> SEQUENCE: 40

Pro Leu Asn Met Thr His Ser Pro Ile Thr
1               5                   10

<210> SEQ ID NO 41

```
<211> LENGTH: 10
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 41

Pro Leu Asn Met Thr His Ser Pro Val Thr
1               5                   10

<210> SEQ ID NO 42
<211> LENGTH: 10
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 42

Pro Val Asn Met Thr His Ser Pro Ile Thr
1               5                   10

<210> SEQ ID NO 43
<211> LENGTH: 10
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 43

Pro Val Asn Met Thr His Ser Pro Val Thr
1               5                   10

<210> SEQ ID NO 44
<211> LENGTH: 10
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 44

Pro Leu Asn Met Thr His Ser Pro Leu Ser
1               5                   10

<210> SEQ ID NO 45
<211> LENGTH: 10
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 45

Pro Val Asn Met Thr His Ser Pro Leu Ser
1               5                   10

<210> SEQ ID NO 46
<211> LENGTH: 10
<212> TYPE: PRT
<213> ORGANISM: Artificial Sequence
<220> FEATURE:
```

<223> OTHER INFORMATION: synthetic exon 16-deleted human epidermal
      growth factor receptor 2 (HER2delta16) first and second
      peptide monomers with conservative substitutions

<400> SEQUENCE: 46

Pro Leu Asn Cys Ser His Thr Pro Leu Thr
1               5                   10

<210> SEQ ID NO 47
<211> LENGTH: 10
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 47

Pro Val Asn Cys Ser His Thr Pro Leu Thr
1               5                   10

<210> SEQ ID NO 48
<211> LENGTH: 10
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 48

Pro Leu Asn Cys Ser His Ser Pro Ile Thr
1               5                   10

<210> SEQ ID NO 49
<211> LENGTH: 10
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 49

Pro Leu Asn Cys Ser His Ser Pro Val Thr
1               5                   10

<210> SEQ ID NO 50
<211> LENGTH: 10
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 50

Pro Val Asn Cys Ser His Ser Pro Ile Thr
1               5                   10

<210> SEQ ID NO 51
<211> LENGTH: 10
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

```
<400> SEQUENCE: 51

Pro Val Asn Cys Ser His Ser Pro Val Thr
1               5                   10

<210> SEQ ID NO 52
<211> LENGTH: 10
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 52

Pro Leu Asn Cys Ser His Ser Pro Leu Ser
1               5                   10

<210> SEQ ID NO 53
<211> LENGTH: 10
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 53

Pro Val Asn Cys Ser His Ser Pro Leu Ser
1               5                   10

<210> SEQ ID NO 54
<211> LENGTH: 10
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 54

Pro Leu Asn Cys Thr His Thr Pro Ile Thr
1               5                   10

<210> SEQ ID NO 55
<211> LENGTH: 10
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 55

Pro Leu Asn Cys Thr His Thr Pro Val Thr
1               5                   10

<210> SEQ ID NO 56
<211> LENGTH: 10
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 56

Pro Val Asn Cys Thr His Thr Pro Ile Thr
1               5                   10
```

<210> SEQ ID NO 57
<211> LENGTH: 10
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 57

Pro Val Asn Cys Thr His Thr Pro Val Thr
1               5                   10

<210> SEQ ID NO 58
<211> LENGTH: 10
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 58

Pro Leu Asn Cys Thr His Ser Pro Ile Ser
1               5                   10

<210> SEQ ID NO 59
<211> LENGTH: 10
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 59

Pro Leu Asn Cys Thr His Ser Pro Val Ser
1               5                   10

<210> SEQ ID NO 60
<211> LENGTH: 10
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 60

Pro Val Asn Cys Thr His Ser Pro Ile Ser
1               5                   10

<210> SEQ ID NO 61
<211> LENGTH: 10
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 61

Pro Val Asn Cys Thr His Ser Pro Val Ser
1               5                   10

<210> SEQ ID NO 62
<211> LENGTH: 11

```
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 62

Cys Pro Ile Asn Cys Thr His Ser Pro Leu Thr
1               5                   10

<210> SEQ ID NO 63
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 63

Cys Pro Leu Asn Cys Thr His Ser Pro Leu Thr
1               5                   10

<210> SEQ ID NO 64
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 64

Cys Pro Val Asn Cys Thr His Ser Pro Leu Thr
1               5                   10

<210> SEQ ID NO 65
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 65

Cys Pro Ile Asn Met Thr His Ser Pro Leu Thr
1               5                   10

<210> SEQ ID NO 66
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 66

Cys Pro Ile Asn Cys Ser His Ser Pro Leu Thr
1               5                   10

<210> SEQ ID NO 67
<211> LENGTH: 11
<212> TYPE: PRT
<213> ORGANISM: Artificial Sequence
<220> FEATURE:
<223> OTHER INFORMATION: synthetic exon 16-deleted human epidermal
``` growth factor receptor 2 (HER2delta16) first and second
peptide monomers with conservative substitutions

<400> SEQUENCE: 67

Cys Pro Ile Asn Cys Thr His Thr Pro Leu Thr
1               5                   10

<210> SEQ ID NO 68
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 68

Cys Pro Ile Asn Cys Thr His Ser Pro Ile Thr
1               5                   10

<210> SEQ ID NO 69
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 69

Cys Pro Ile Asn Cys Thr His Ser Pro Val Thr
1               5                   10

<210> SEQ ID NO 70
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 70

Cys Pro Ile Asn Cys Thr His Ser Pro Leu Ser
1               5                   10

<210> SEQ ID NO 71
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 71

Cys Pro Leu Asn Met Thr His Ser Pro Leu Thr
1               5                   10

<210> SEQ ID NO 72
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 72

Cys Pro Val Asn Met Thr His Ser Pro Leu Thr
1               5                   10

<210> SEQ ID NO 73
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 73

Cys Pro Leu Asn Cys Ser His Ser Pro Leu Thr
1               5                   10

<210> SEQ ID NO 74
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 74

Cys Pro Val Asn Cys Ser His Ser Pro Leu Thr
1               5                   10

<210> SEQ ID NO 75
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 75

Cys Pro Leu Asn Cys Thr His Thr Pro Leu Thr
1               5                   10

<210> SEQ ID NO 76
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 76

Cys Pro Val Asn Cys Thr His Thr Pro Leu Thr
1               5                   10

<210> SEQ ID NO 77
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 77

Cys Pro Leu Asn Cys Thr His Ser Pro Ile Thr
1               5                   10

<210> SEQ ID NO 78
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 78

Cys Pro Val Asn Cys Thr His Ser Pro Ile Thr
 1               5                  10

<210> SEQ ID NO 79
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 79

Cys Pro Leu Asn Cys Thr His Ser Pro Val Thr
 1               5                  10

<210> SEQ ID NO 80
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 80

Cys Pro Val Asn Cys Thr His Ser Pro Val Thr
 1               5                  10

<210> SEQ ID NO 81
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 81

Cys Pro Leu Asn Cys Thr His Ser Pro Leu Ser
 1               5                  10

<210> SEQ ID NO 82
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 82

Cys Pro Val Asn Cys Thr His Ser Pro Leu Ser
 1               5                  10

<210> SEQ ID NO 83
<211> LENGTH: 11
<212> TYPE: PRT

-continued

```
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 83

Cys Pro Ile Asn Met Ser His Ser Pro Leu Thr
1               5                   10

<210> SEQ ID NO 84
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 84

Cys Pro Ile Asn Met Thr His Thr Pro Leu Thr
1               5                   10

<210> SEQ ID NO 85
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 85

Cys Pro Ile Asn Met Thr His Ser Pro Ile Thr
1               5                   10

<210> SEQ ID NO 86
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 86

Cys Pro Ile Asn Met Thr His Ser Pro Val Thr
1               5                   10

<210> SEQ ID NO 87
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 87

Cys Pro Ile Asn Met Thr His Ser Pro Leu Ser
1               5                   10

<210> SEQ ID NO 88
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
``` peptide monomers with conservative substitutions

<400> SEQUENCE: 88

Cys Pro Ile Asn Cys Ser His Thr Pro Leu Thr
1               5                   10

<210> SEQ ID NO 89
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 89

Cys Pro Ile Asn Cys Ser His Ser Pro Ile Thr
1               5                   10

<210> SEQ ID NO 90
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 90

Cys Pro Ile Asn Cys Ser His Ser Pro Val Thr
1               5                   10

<210> SEQ ID NO 91
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 91

Cys Pro Ile Asn Cys Ser His Ser Pro Leu Ser
1               5                   10

<210> SEQ ID NO 92
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 92

Cys Pro Ile Asn Cys Thr His Thr Pro Ile Thr
1               5                   10

<210> SEQ ID NO 93
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 93

Cys Pro Ile Asn Cys Thr His Thr Pro Val Thr
1               5                   10

<210> SEQ ID NO 94
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 94

Cys Pro Ile Asn Cys Thr His Thr Pro Leu Ser
1               5                   10

<210> SEQ ID NO 95
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 95

Cys Pro Ile Asn Cys Thr His Ser Pro Ile Ser
1               5                   10

<210> SEQ ID NO 96
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 96

Cys Pro Ile Asn Cys Thr His Ser Pro Val Ser
1               5                   10

<210> SEQ ID NO 97
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 97

Cys Pro Leu Asn Met Ser His Ser Pro Leu Thr
1               5                   10

<210> SEQ ID NO 98
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 98

Cys Pro Val Asn Met Ser His Ser Pro Leu Thr
1               5                   10

```
<210> SEQ ID NO 99
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 99

Cys Pro Leu Asn Met Thr His Thr Pro Leu Thr
1               5                   10

<210> SEQ ID NO 100
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 100

Cys Pro Val Asn Met Thr His Thr Pro Leu Thr
1               5                   10

<210> SEQ ID NO 101
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 101

Cys Pro Leu Asn Met Thr His Ser Pro Ile Thr
1               5                   10

<210> SEQ ID NO 102
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 102

Cys Pro Leu Asn Met Thr His Ser Pro Val Thr
1               5                   10

<210> SEQ ID NO 103
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 103

Cys Pro Val Asn Met Thr His Ser Pro Ile Thr
1               5                   10

<210> SEQ ID NO 104
<211> LENGTH: 11
<212> TYPE: PRT
<213> ORGANISM: Artificial Sequence
```

```
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 104

Cys Pro Val Asn Met Thr His Ser Pro Val Thr
1               5                   10

<210> SEQ ID NO 105
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 105

Cys Pro Leu Asn Met Thr His Ser Pro Leu Ser
1               5                   10

<210> SEQ ID NO 106
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 106

Cys Pro Val Asn Met Thr His Ser Pro Leu Ser
1               5                   10

<210> SEQ ID NO 107
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 107

Cys Pro Leu Asn Cys Ser His Thr Pro Leu Thr
1               5                   10

<210> SEQ ID NO 108
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 108

Cys Pro Val Asn Cys Ser His Thr Pro Leu Thr
1               5                   10

<210> SEQ ID NO 109
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions
```

<400> SEQUENCE: 109

Cys Pro Leu Asn Cys Ser His Ser Pro Ile Thr
1               5                   10

<210> SEQ ID NO 110
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 110

Cys Pro Leu Asn Cys Ser His Ser Pro Val Thr
1               5                   10

<210> SEQ ID NO 111
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 111

Cys Pro Val Asn Cys Ser His Ser Pro Ile Thr
1               5                   10

<210> SEQ ID NO 112
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 112

Cys Pro Val Asn Cys Ser His Ser Pro Val Thr
1               5                   10

<210> SEQ ID NO 113
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 113

Cys Pro Leu Asn Cys Ser His Ser Pro Leu Ser
1               5                   10

<210> SEQ ID NO 114
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 114

Cys Pro Val Asn Cys Ser His Ser Pro Leu Ser

<210> SEQ ID NO 115
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 115

Cys Pro Leu Asn Cys Thr His Thr Pro Ile Thr
1               5                   10

<210> SEQ ID NO 116
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 116

Cys Pro Leu Asn Cys Thr His Thr Pro Val Thr
1               5                   10

<210> SEQ ID NO 117
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 117

Cys Pro Val Asn Cys Thr His Thr Pro Ile Thr
1               5                   10

<210> SEQ ID NO 118
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 118

Cys Pro Val Asn Cys Thr His Thr Pro Val Thr
1               5                   10

<210> SEQ ID NO 119
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 119

Cys Pro Leu Asn Cys Thr His Ser Pro Ile Ser
1               5                   10

<210> SEQ ID NO 120

```
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 120

Cys Pro Leu Asn Cys Thr His Ser Pro Val Ser
1               5                   10

<210> SEQ ID NO 121
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 121

Cys Pro Val Asn Cys Thr His Ser Pro Ile Ser
1               5                   10

<210> SEQ ID NO 122
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 122

Cys Pro Val Asn Cys Thr His Ser Pro Val Ser
1               5                   10

<210> SEQ ID NO 123
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 123

Pro Ile Asn Cys Thr His Ser Pro Leu Thr Ser
1               5                   10

<210> SEQ ID NO 124
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 124

Pro Leu Asn Cys Thr His Ser Pro Leu Thr Ser
1               5                   10

<210> SEQ ID NO 125
<211> LENGTH: 11
<212> TYPE: PRT
<213> ORGANISM: Artificial Sequence
<220> FEATURE:
```

```
<223> OTHER INFORMATION: synthetic exon 16-deleted human epidermal
      growth factor receptor 2 (HER2delta16) first and second
      peptide monomers with conservative substitutions

<400> SEQUENCE: 125

Pro Val Asn Cys Thr His Ser Pro Leu Thr Ser
1               5                   10

<210> SEQ ID NO 126
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 126

Pro Ile Asn Met Thr His Ser Pro Leu Thr Ser
1               5                   10

<210> SEQ ID NO 127
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 127

Pro Ile Asn Cys Ser His Ser Pro Leu Thr Ser
1               5                   10

<210> SEQ ID NO 128
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 128

Pro Ile Asn Cys Thr His Thr Pro Leu Thr Ser
1               5                   10

<210> SEQ ID NO 129
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 129

Pro Ile Asn Cys Thr His Ser Pro Ile Thr Ser
1               5                   10

<210> SEQ ID NO 130
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions
```

```
<400> SEQUENCE: 130

Pro Ile Asn Cys Thr His Ser Pro Val Thr Ser
1               5                   10

<210> SEQ ID NO 131
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 131

Pro Ile Asn Cys Thr His Ser Pro Leu Ser Ser
1               5                   10

<210> SEQ ID NO 132
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 132

Pro Leu Asn Met Thr His Ser Pro Leu Thr Ser
1               5                   10

<210> SEQ ID NO 133
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 133

Pro Val Asn Met Thr His Ser Pro Leu Thr Ser
1               5                   10

<210> SEQ ID NO 134
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 134

Pro Leu Asn Cys Ser His Ser Pro Leu Thr Ser
1               5                   10

<210> SEQ ID NO 135
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 135

Pro Val Asn Cys Ser His Ser Pro Leu Thr Ser
1               5                   10
```

<210> SEQ ID NO 136
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 136

Pro Leu Asn Cys Thr His Thr Pro Leu Thr Ser
1               5                   10

<210> SEQ ID NO 137
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 137

Pro Val Asn Cys Thr His Thr Pro Leu Thr Ser
1               5                   10

<210> SEQ ID NO 138
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 138

Pro Leu Asn Cys Thr His Ser Pro Ile Thr Ser
1               5                   10

<210> SEQ ID NO 139
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 139

Pro Val Asn Cys Thr His Ser Pro Ile Thr Ser
1               5                   10

<210> SEQ ID NO 140
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 140

Pro Leu Asn Cys Thr His Ser Pro Val Thr Ser
1               5                   10

<210> SEQ ID NO 141
<211> LENGTH: 11

```
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 141

Pro Val Asn Cys Thr His Ser Pro Val Thr Ser
1               5                   10

<210> SEQ ID NO 142
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 142

Pro Leu Asn Cys Thr His Ser Pro Leu Ser Ser
1               5                   10

<210> SEQ ID NO 143
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 143

Pro Val Asn Cys Thr His Ser Pro Leu Ser Ser
1               5                   10

<210> SEQ ID NO 144
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 144

Pro Ile Asn Met Ser His Ser Pro Leu Thr Ser
1               5                   10

<210> SEQ ID NO 145
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 145

Pro Ile Asn Met Thr His Thr Pro Leu Thr Ser
1               5                   10

<210> SEQ ID NO 146
<211> LENGTH: 11
<212> TYPE: PRT
<213> ORGANISM: Artificial Sequence
<220> FEATURE:
<223> OTHER INFORMATION: synthetic exon 16-deleted human epidermal
```

-continued growth factor receptor 2 (HER2delta16) first and second
peptide monomers with conservative substitutions

<400> SEQUENCE: 146

Pro Ile Asn Met Thr His Ser Pro Ile Thr Ser
1               5                   10

<210> SEQ ID NO 147
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 147

Pro Ile Asn Met Thr His Ser Pro Val Thr Ser
1               5                   10

<210> SEQ ID NO 148
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 148

Pro Ile Asn Met Thr His Ser Pro Leu Ser Ser
1               5                   10

<210> SEQ ID NO 149
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 149

Pro Ile Asn Cys Ser His Thr Pro Leu Thr Ser
1               5                   10

<210> SEQ ID NO 150
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 150

Pro Ile Asn Cys Ser His Ser Pro Ile Thr Ser
1               5                   10

<210> SEQ ID NO 151
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 151

Pro Ile Asn Cys Ser His Ser Pro Val Thr Ser
1               5                   10

<210> SEQ ID NO 152
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 152

Pro Ile Asn Cys Ser His Ser Pro Leu Ser Ser
1               5                   10

<210> SEQ ID NO 153
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 153

Pro Ile Asn Cys Thr His Thr Pro Ile Thr Ser
1               5                   10

<210> SEQ ID NO 154
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 154

Pro Ile Asn Cys Thr His Thr Pro Val Thr Ser
1               5                   10

<210> SEQ ID NO 155
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 155

Pro Ile Asn Cys Thr His Thr Pro Leu Ser Ser
1               5                   10

<210> SEQ ID NO 156
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 156

Pro Ile Asn Cys Thr His Ser Pro Ile Ser Ser
1               5                   10

<210> SEQ ID NO 157
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 157

Pro Ile Asn Cys Thr His Ser Pro Val Ser Ser
1               5                   10

<210> SEQ ID NO 158
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 158

Pro Leu Asn Met Ser His Ser Pro Leu Thr Ser
1               5                   10

<210> SEQ ID NO 159
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 159

Pro Val Asn Met Ser His Ser Pro Leu Thr Ser
1               5                   10

<210> SEQ ID NO 160
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 160

Pro Leu Asn Met Thr His Thr Pro Leu Thr Ser
1               5                   10

<210> SEQ ID NO 161
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 161

Pro Val Asn Met Thr His Thr Pro Leu Thr Ser
1               5                   10

<210> SEQ ID NO 162
<211> LENGTH: 11
<212> TYPE: PRT

<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 162

Pro Leu Asn Met Thr His Ser Pro Ile Thr Ser
1               5                   10

<210> SEQ ID NO 163
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 163

Pro Leu Asn Met Thr His Ser Pro Val Thr Ser
1               5                   10

<210> SEQ ID NO 164
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 164

Pro Val Asn Met Thr His Ser Pro Ile Thr Ser
1               5                   10

<210> SEQ ID NO 165
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 165

Pro Val Asn Met Thr His Ser Pro Val Thr Ser
1               5                   10

<210> SEQ ID NO 166
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 166

Pro Leu Asn Met Thr His Ser Pro Leu Ser Ser
1               5                   10

<210> SEQ ID NO 167
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second

```
      peptide monomers with conservative substitutions

<400> SEQUENCE: 167

Pro Val Asn Met Thr His Ser Pro Leu Ser Ser
1               5                   10

<210> SEQ ID NO 168
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 168

Pro Leu Asn Cys Ser His Thr Pro Leu Thr Ser
1               5                   10

<210> SEQ ID NO 169
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 169

Pro Val Asn Cys Ser His Thr Pro Leu Thr Ser
1               5                   10

<210> SEQ ID NO 170
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 170

Pro Leu Asn Cys Ser His Ser Pro Ile Thr Ser
1               5                   10

<210> SEQ ID NO 171
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 171

Pro Leu Asn Cys Ser His Ser Pro Val Thr Ser
1               5                   10

<210> SEQ ID NO 172
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 172
```

```
Pro Val Asn Cys Ser His Ser Pro Ile Thr Ser
1               5                   10
```

<210> SEQ ID NO 173
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 173

```
Pro Val Asn Cys Ser His Ser Pro Val Thr Ser
1               5                   10
```

<210> SEQ ID NO 174
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 174

```
Pro Leu Asn Cys Ser His Ser Pro Leu Ser Ser
1               5                   10
```

<210> SEQ ID NO 175
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 175

```
Pro Val Asn Cys Ser His Ser Pro Leu Ser Ser
1               5                   10
```

<210> SEQ ID NO 176
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 176

```
Pro Leu Asn Cys Thr His Thr Pro Ile Thr Ser
1               5                   10
```

<210> SEQ ID NO 177
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 177

```
Pro Leu Asn Cys Thr His Thr Pro Val Thr Ser
1               5                   10
```

-continued

<210> SEQ ID NO 178
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 178

Pro Val Asn Cys Thr His Thr Pro Ile Thr Ser
1               5                   10

<210> SEQ ID NO 179
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 179

Pro Val Asn Cys Thr His Thr Pro Val Thr Ser
1               5                   10

<210> SEQ ID NO 180
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 180

Pro Leu Asn Cys Thr His Ser Pro Ile Ser Ser
1               5                   10

<210> SEQ ID NO 181
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 181

Pro Leu Asn Cys Thr His Ser Pro Val Ser Ser
1               5                   10

<210> SEQ ID NO 182
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 182

Pro Val Asn Cys Thr His Ser Pro Ile Ser Ser
1               5                   10

<210> SEQ ID NO 183
<211> LENGTH: 11
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 183

Pro Val Asn Cys Thr His Ser Pro Val Ser Ser
1               5                   10

<210> SEQ ID NO 184
<211> LENGTH: 12
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 184

Cys Pro Ile Asn Cys Thr His Ser Pro Leu Thr Ser
1               5                   10

<210> SEQ ID NO 185
<211> LENGTH: 12
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 185

Cys Pro Leu Asn Cys Thr His Ser Pro Leu Thr Ser
1               5                   10

<210> SEQ ID NO 186
<211> LENGTH: 12
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 186

Cys Pro Val Asn Cys Thr His Ser Pro Leu Thr Ser
1               5                   10

<210> SEQ ID NO 187
<211> LENGTH: 12
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 187

Cys Pro Ile Asn Met Thr His Ser Pro Leu Thr Ser
1               5                   10

<210> SEQ ID NO 188
<211> LENGTH: 12
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 188

Cys Pro Ile Asn Cys Ser His Ser Pro Leu Thr Ser
1               5                   10

<210> SEQ ID NO 189
<211> LENGTH: 12
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 189

Cys Pro Ile Asn Cys Thr His Thr Pro Leu Thr Ser
1               5                   10

<210> SEQ ID NO 190
<211> LENGTH: 12
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 190

Cys Pro Ile Asn Cys Thr His Ser Pro Ile Thr Ser
1               5                   10

<210> SEQ ID NO 191
<211> LENGTH: 12
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 191

Cys Pro Ile Asn Cys Thr His Ser Pro Val Thr Ser
1               5                   10

<210> SEQ ID NO 192
<211> LENGTH: 12
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 192

Cys Pro Ile Asn Cys Thr His Ser Pro Leu Ser Ser
1               5                   10

<210> SEQ ID NO 193
<211> LENGTH: 12
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 193

Cys Pro Leu Asn Met Thr His Ser Pro Leu Thr Ser

-continued

```
1               5                   10

<210> SEQ ID NO 194
<211> LENGTH: 12
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 194

Cys Pro Val Asn Met Thr His Ser Pro Leu Thr Ser
1               5                   10

<210> SEQ ID NO 195
<211> LENGTH: 12
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 195

Cys Pro Leu Asn Cys Ser His Ser Pro Leu Thr Ser
1               5                   10

<210> SEQ ID NO 196
<211> LENGTH: 12
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 196

Cys Pro Val Asn Cys Ser His Ser Pro Leu Thr Ser
1               5                   10

<210> SEQ ID NO 197
<211> LENGTH: 12
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 197

Cys Pro Leu Asn Cys Thr His Thr Pro Leu Thr Ser
1               5                   10

<210> SEQ ID NO 198
<211> LENGTH: 12
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 198

Cys Pro Val Asn Cys Thr His Thr Pro Leu Thr Ser
1               5                   10

<210> SEQ ID NO 199
```

```
<211> LENGTH: 12
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 199

Cys Pro Leu Asn Cys Thr His Ser Pro Ile Thr Ser
 1               5                   10

<210> SEQ ID NO 200
<211> LENGTH: 12
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 200

Cys Pro Val Asn Cys Thr His Ser Pro Ile Thr Ser
 1               5                   10

<210> SEQ ID NO 201
<211> LENGTH: 12
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 201

Cys Pro Leu Asn Cys Thr His Ser Pro Val Thr Ser
 1               5                   10

<210> SEQ ID NO 202
<211> LENGTH: 12
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 202

Cys Pro Val Asn Cys Thr His Ser Pro Val Thr Ser
 1               5                   10

<210> SEQ ID NO 203
<211> LENGTH: 12
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 203

Cys Pro Leu Asn Cys Thr His Ser Pro Leu Ser Ser
 1               5                   10

<210> SEQ ID NO 204
<211> LENGTH: 12
<212> TYPE: PRT
<213> ORGANISM: Artificial Sequence
<220> FEATURE:
```

```
<223> OTHER INFORMATION: synthetic exon 16-deleted human epidermal
      growth factor receptor 2 (HER2delta16) first and second
      peptide monomers with conservative substitutions

<400> SEQUENCE: 204

Cys Pro Val Asn Cys Thr His Ser Pro Leu Ser Ser
1               5                   10

<210> SEQ ID NO 205
<211> LENGTH: 12
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 205

Cys Pro Ile Asn Met Ser His Ser Pro Leu Thr Ser
1               5                   10

<210> SEQ ID NO 206
<211> LENGTH: 12
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 206

Cys Pro Ile Asn Met Thr His Thr Pro Leu Thr Ser
1               5                   10

<210> SEQ ID NO 207
<211> LENGTH: 12
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 207

Cys Pro Ile Asn Met Thr His Ser Pro Ile Thr Ser
1               5                   10

<210> SEQ ID NO 208
<211> LENGTH: 12
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 208

Cys Pro Ile Asn Met Thr His Ser Pro Val Thr Ser
1               5                   10

<210> SEQ ID NO 209
<211> LENGTH: 12
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions
```

```
<400> SEQUENCE: 209

Cys Pro Ile Asn Met Thr His Ser Pro Leu Ser Ser
1               5                   10

<210> SEQ ID NO 210
<211> LENGTH: 12
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 210

Cys Pro Ile Asn Cys Ser His Thr Pro Leu Thr Ser
1               5                   10

<210> SEQ ID NO 211
<211> LENGTH: 12
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 211

Cys Pro Ile Asn Cys Ser His Ser Pro Ile Thr Ser
1               5                   10

<210> SEQ ID NO 212
<211> LENGTH: 12
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 212

Cys Pro Ile Asn Cys Ser His Ser Pro Val Thr Ser
1               5                   10

<210> SEQ ID NO 213
<211> LENGTH: 12
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 213

Cys Pro Ile Asn Cys Ser His Ser Pro Leu Ser Ser
1               5                   10

<210> SEQ ID NO 214
<211> LENGTH: 12
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 214

Cys Pro Ile Asn Cys Thr His Thr Pro Ile Thr Ser
1               5                   10
```

<210> SEQ ID NO 215
<211> LENGTH: 12
<212> TYPE: PRT
<213> ORGANISM: Artificial Sequence
<220> FEATURE:
<223> OTHER INFORMATION: synthetic exon 16-deleted human epidermal growth factor receptor 2 (HER2delta16) first and second peptide monomers with conservative substitutions

<400> SEQUENCE: 215

Cys Pro Ile Asn Cys Thr His Thr Pro Val Thr Ser
1               5                   10

<210> SEQ ID NO 216
<211> LENGTH: 12
<212> TYPE: PRT
<213> ORGANISM: Artificial Sequence
<220> FEATURE:
<223> OTHER INFORMATION: synthetic exon 16-deleted human epidermal growth factor receptor 2 (HER2delta16) first and second peptide monomers with conservative substitutions

<400> SEQUENCE: 216

Cys Pro Ile Asn Cys Thr His Thr Pro Leu Ser Ser
1               5                   10

<210> SEQ ID NO 217
<211> LENGTH: 12
<212> TYPE: PRT
<213> ORGANISM: Artificial Sequence
<220> FEATURE:
<223> OTHER INFORMATION: synthetic exon 16-deleted human epidermal growth factor receptor 2 (HER2delta16) first and second peptide monomers with conservative substitutions

<400> SEQUENCE: 217

Cys Pro Ile Asn Cys Thr His Ser Pro Ile Ser Ser
1               5                   10

<210> SEQ ID NO 218
<211> LENGTH: 12
<212> TYPE: PRT
<213> ORGANISM: Artificial Sequence
<220> FEATURE:
<223> OTHER INFORMATION: synthetic exon 16-deleted human epidermal growth factor receptor 2 (HER2delta16) first and second peptide monomers with conservative substitutions

<400> SEQUENCE: 218

Cys Pro Ile Asn Cys Thr His Ser Pro Val Ser Ser
1               5                   10

<210> SEQ ID NO 219
<211> LENGTH: 12
<212> TYPE: PRT
<213> ORGANISM: Artificial Sequence
<220> FEATURE:
<223> OTHER INFORMATION: synthetic exon 16-deleted human epidermal growth factor receptor 2 (HER2delta16) first and second peptide monomers with conservative substitutions

<400> SEQUENCE: 219

Cys Pro Leu Asn Met Ser His Ser Pro Leu Thr Ser
1               5                   10

<210> SEQ ID NO 220
<211> LENGTH: 12

```
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 220

Cys Pro Val Asn Met Ser His Ser Pro Leu Thr Ser
1               5                   10

<210> SEQ ID NO 221
<211> LENGTH: 12
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 221

Cys Pro Leu Asn Met Thr His Thr Pro Leu Thr Ser
1               5                   10

<210> SEQ ID NO 222
<211> LENGTH: 12
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 222

Cys Pro Val Asn Met Thr His Thr Pro Leu Thr Ser
1               5                   10

<210> SEQ ID NO 223
<211> LENGTH: 12
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 223

Cys Pro Leu Asn Met Thr His Ser Pro Ile Thr Ser
1               5                   10

<210> SEQ ID NO 224
<211> LENGTH: 12
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 224

Cys Pro Leu Asn Met Thr His Ser Pro Val Thr Ser
1               5                   10

<210> SEQ ID NO 225
<211> LENGTH: 12
<212> TYPE: PRT
<213> ORGANISM: Artificial Sequence
<220> FEATURE:
<223> OTHER INFORMATION: synthetic exon 16-deleted human epidermal
```

-continued growth factor receptor 2 (HER2delta16) first and second
peptide monomers with conservative substitutions

<400> SEQUENCE: 225

Cys Pro Val Asn Met Thr His Ser Pro Ile Thr Ser
1               5                   10

<210> SEQ ID NO 226
<211> LENGTH: 12
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 226

Cys Pro Val Asn Met Thr His Ser Pro Val Thr Ser
1               5                   10

<210> SEQ ID NO 227
<211> LENGTH: 12
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 227

Cys Pro Leu Asn Met Thr His Ser Pro Leu Ser Ser
1               5                   10

<210> SEQ ID NO 228
<211> LENGTH: 12
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 228

Cys Pro Val Asn Met Thr His Ser Pro Leu Ser Ser
1               5                   10

<210> SEQ ID NO 229
<211> LENGTH: 12
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 229

Cys Pro Leu Asn Cys Ser His Thr Pro Leu Thr Ser
1               5                   10

<210> SEQ ID NO 230
<211> LENGTH: 12
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 230

```
Cys Pro Val Asn Cys Ser His Thr Pro Leu Thr Ser
1               5                   10
```

<210> SEQ ID NO 231
<211> LENGTH: 12
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 231

```
Cys Pro Leu Asn Cys Ser His Ser Pro Ile Thr Ser
1               5                   10
```

<210> SEQ ID NO 232
<211> LENGTH: 12
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 232

```
Cys Pro Leu Asn Cys Ser His Ser Pro Val Thr Ser
1               5                   10
```

<210> SEQ ID NO 233
<211> LENGTH: 12
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 233

```
Cys Pro Val Asn Cys Ser His Ser Pro Ile Thr Ser
1               5                   10
```

<210> SEQ ID NO 234
<211> LENGTH: 12
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 234

```
Cys Pro Val Asn Cys Ser His Ser Pro Val Thr Ser
1               5                   10
```

<210> SEQ ID NO 235
<211> LENGTH: 12
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 235

```
Cys Pro Leu Asn Cys Ser His Ser Pro Leu Ser Ser
1               5                   10
```

<210> SEQ ID NO 236
<211> LENGTH: 12
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 236

Cys Pro Val Asn Cys Ser His Ser Pro Leu Ser Ser
1               5                   10

<210> SEQ ID NO 237
<211> LENGTH: 12
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 237

Cys Pro Leu Asn Cys Thr His Thr Pro Ile Thr Ser
1               5                   10

<210> SEQ ID NO 238
<211> LENGTH: 12
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 238

Cys Pro Leu Asn Cys Thr His Thr Pro Val Thr Ser
1               5                   10

<210> SEQ ID NO 239
<211> LENGTH: 12
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 239

Cys Pro Val Asn Cys Thr His Thr Pro Ile Thr Ser
1               5                   10

<210> SEQ ID NO 240
<211> LENGTH: 12
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 240

Cys Pro Val Asn Cys Thr His Thr Pro Val Thr Ser
1               5                   10

<210> SEQ ID NO 241
<211> LENGTH: 12
<212> TYPE: PRT

```
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 241

Cys Pro Leu Asn Cys Thr His Ser Pro Ile Ser Ser
1               5                   10

<210> SEQ ID NO 242
<211> LENGTH: 12
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 242

Cys Pro Leu Asn Cys Thr His Ser Pro Val Ser Ser
1               5                   10

<210> SEQ ID NO 243
<211> LENGTH: 12
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 243

Cys Pro Val Asn Cys Thr His Ser Pro Ile Ser Ser
1               5                   10

<210> SEQ ID NO 244
<211> LENGTH: 12
<212> TYPE: PRT
<213> ORGANISM: Artificial Sequence
<220> FEATURE:
<223> OTHER INFORMATION: synthetic exon 16-deleted human epidermal
      growth factor receptor 2 (HER2delta16) first and second
      peptide monomers with conservative substitutions

<400> SEQUENCE: 244

Cys Pro Val Asn Cys Thr His Ser Pro Val Ser Ser
1               5                   10

<210> SEQ ID NO 245
<211> LENGTH: 27
<212> TYPE: PRT
<213> ORGANISM: Artificial Sequence
<220> FEATURE:
<223> OTHER INFORMATION: synthetic peptide #1 for detecting wild-type
      HER2, exon 16-deleted human epidermal growth factor
      receptor 2 (HER2delta16) cyclic peptide
<220> FEATURE:
<221> NAME/KEY: MOD_RES
<222> LOCATION: (1)...(1)
<223> OTHER INFORMATION: Pro modified by beta-mercaptopropionic acid
      (MPA)
<220> FEATURE:
<221> NAME/KEY: DISULFID
<222> LOCATION: (1)...(9)
<223> OTHER INFORMATION: beta-mercaptopropionic acid (MPA) of modified
      Pro at position 1 linked by disulfide bond to Cys at position 8
<220> FEATURE:
<221> NAME/KEY: DISULFID
<222> LOCATION: (4)...(16)
<223> OTHER INFORMATION: Cys-Cys disulfide bond
```

```
-continued

<220> FEATURE:
<221> NAME/KEY: AMIDATION
<222> LOCATION: (27)...(27)
<223> OTHER INFORMATION: Xaa = lysinamide, ornithinamide,
      beta-amino-alaninamide, alpha,gamma-diamino-butyric acid amide or
      2,7-diamino-heptanoic acid amide

<400> SEQUENCE: 245

Pro Ile Asn Cys Thr His Ser Cys Val Asp Leu Asp Lys Gly Cys
1               5                   10                  15

Pro Ala Glu Gln Arg Ala Ser Pro Leu Thr Xaa
            20                  25
```

HER2DELTA16 PEPTIDES

CROSS-REFERENCE TO RELATED APPLICATIONS

The present application is a continuation of U.S. patent application Ser. No. 14/712,165, filed May 14, 2015, which issued on Apr. 25, 2017 as U.S. Pat. No. 9,630,993 B2, which is a continuation of U.S. patent application Ser. No. 13/901,210, filed May 23, 2013, issued on Jun. 23, 2015 as U.S. Pat. No. 9,062,096, which is a continuation of PCT/US2011/062954 filed Dec. 1, 2011, which application claims priority to U.S. Provisional Application No. 61/419,210, filed Dec. 2, 2010, the disclosures of each of which are hereby incorporated by reference in their entirety for all purposes.

STATEMENT REGARDING SEQUENCE LISTING

The Sequence Listing written in file 67295000_1.txt created on Jun. 27, 2017, 85,301 bytes, machine format IBM-PC, MS-Windows operating system, is hereby incorporated by reference in its entirety for all purposes.

BACKGROUND OF THE INVENTION

Human epidermal growth factor receptor 2 (HER2) HER2 is overexpressed in approximately 25% of human breast cancers and is associated with a poorer clinical outcome as compared to breast cancers in which HER2 is not overexpressed. Much research has focused on developing therapies that specifically target HER2 and its signaling pathway. Examples of HER2-targeted therapies include trastuzumab, a monoclonal antibody that may be used alone or in combination with other therapeutic agents, and lapatinib, a small molecule tyrosine kinase inhibitor that is used in combination with other therapeutic agents.

Although the HER2-targeted therapy trastuzumab is widely used to treat patients who have HER2-overexpressing metastatic breast tumors, a significant number of patients fail to respond to trastuzumab treatment, and some patients who initially respond to the treatment regress within six months of the onset of treatment. It has been proposed that expression of an oncogenic isoform of HER2 called HER2Δ16 is involved in trastuzumab-refractory breast cancer (Mitra et al., *Mol. Cancer Ther.* 8(8):2152-2162 (2009)). HER2Δ16 is a splice variant of HER2 that lacks exon 16 and that, unlike HER2, is not expressed in normal (non-malignant) human tissues. While HER2 exists predominantly in monomeric form, HER2Δ16 in breast tumor cells exists as a stable, disulfide-linked homodimer. This HER2Δ16 homodimer activates multiple oncogenic signaling pathways, including the FAK, Src kinase, phosphatidylinositol 3-kinase/AKT, and mitogen-activated protein kinase pathways, in contrast to HER2, which only marginally activates each of these signaling pathways. HER2Δ16 expression is significantly associated with lymph node-positive breast cancer, a predictor of negative prognosis in breast cancer, and in vitro studies demonstrate that HER2Δ16 expression promotes cell proliferation, migration, and invasion of tumor cells. Additionally, breast tumor cells that overexpress HER2Δ16 exhibit trastuzumab resistance or even increased proliferation and invasion (Mitra et al., *Mol. Cancer Ther.* 8(8):2152-2162 (2009)).

Because HER2Δ16 expression is associated with enhanced cell tumorigenicity, activation of multiple oncogenic signaling pathways, and resistance to HER2-targeted trastuzumab treatment, patients expressing HER2Δ16 will require different and likely more aggressive therapeutic treatments if treatment is to be successful. Accordingly, there is a need in the art for compositions which will enable the development of assays for specifically detecting the presence of HER2Δ16 homodimers in samples of interest. The present invention satisfies this need and provides related advantages as well.

BRIEF SUMMARY OF THE INVENTION

The present invention provides cyclic peptides comprising a dimer of first and second peptides, each of the first and second peptides comprising a sequence corresponding to an exon 16-deleted HER2 ("HER2Δ16") polypeptide. The present invention also provides antibodies that specifically bind to the HER2Δ16 cyclic peptides and methods of making antibodies that specifically bind to the HER2Δ16 cyclic peptides. The HER2Δ16 cyclic peptides and anti-HER2Δ16 antibodies of the present invention are advantageous, for example, in assays that measure the presence of HER2Δ16 homodimers in a sample, e.g., a sample from a HER2-positive breast tumor patient, and as therapeutic antibodies.

In one aspect, the present invention provides a cyclic peptide comprising a dimer of a first peptide and a second peptide, each of the first and second peptides comprising a sequence corresponding to an exon 16-deleted HER2 ("HER2Δ16") polypeptide, wherein the cyclic peptide is cyclized via (1) one or more disulfide bonds between the first peptide and the second peptide; and/or (2) an amino acid residue $X^1$ linked to an amino acid residue of the first peptide and an amino acid residue of the second peptide.

In some embodiments, each of the first and second peptides independently comprise an amino acid sequence having at least 70% amino acid sequence identity to PINCTHSPLT (SEQ ID NO:1). In some embodiments, each of the first and second peptides has the amino acid sequence PINCTHSPLT (SEQ ID NO:1).

In some embodiments, each of the first and second peptides has an amino acid sequence independently selected from the group consisting of the amino acid sequences listed in Table 1 (i.e., SEQ ID NOs:1-244). In certain preferred embodiments, the first peptide and the second peptide are identical (e.g., SEQ ID NO:1 for the first peptide and SEQ ID NO:1 for the second peptide).

In some embodiments, the cyclized portion of the cyclic peptide comprises from about 15 to about 30 amino acid residues. In some embodiments, the cyclized portion of the cyclic peptide comprises from about 20 to about 25 amino acid residues.

In some embodiments, $X^1$ is linked to the C-terminus of each of the first and second peptides. In some embodiments, $X^1$ is lysine, ornithine, β-amino-alanine, α,γ-diamino-butyric acid, or 2,7-diamino-heptanoic acid.

In some embodiments, each of the first and second peptides further comprises a disulfide bond-forming compound attached to a terminal end of the first or second peptide, wherein the compound attached to the terminal end of the first peptide is linked via a disulfide bond with the compound attached to the terminal end of the second peptide. In some embodiments, the disulfide bond-forming compound is attached to the N-terminus of each of the first and second peptides. In some embodiments, the disulfide bond-forming compound is a cysteine residue or beta-mercaptopropionic acid.

In some embodiments, the cyclic peptide further comprises an amino acid residue $X^2$ linked to the amino acid residue $X^1$. In some embodiments, $X^2$ is lysine, ornithine, β-amino-alanine, α,γ-diamino-butyric acid, or 2,7-diamino-heptanoic acid.

In some embodiments, the cyclic peptide has the formula:

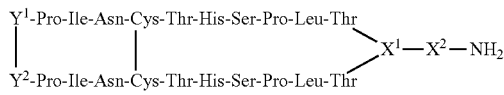

wherein each of $X^1$ and $X^2$ independently is selected from lysine, ornithine, β-amino-alanine, α,γ-diamino-butyric acid, or 2,7-diamino-heptanoic acid;
wherein each of $Y^1$ and $Y^2$ comprises a disulfide bond-forming compound, and wherein $Y^1$ is linked with $Y^2$ via a disulfide bond;
wherein the cysteine residues are linked via a disulfide bond; and
wherein $X^1$ and each Thr are linked via a peptide bond.

In some embodiments, each of $X^1$ and $X^2$ is a lysine. In some embodiments, each of $Y^1$ and $Y^2$ comprises a cysteine residue or beta-mercaptopropionic acid.

In some embodiments, the cyclic peptide has the structure:

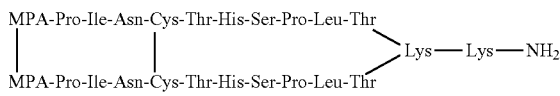

wherein MPA is beta-mercaptopropionic acid.

In some embodiments, the cyclic peptide further comprises a carrier protein conjugated to the cyclic peptide. In some embodiments, the carrier protein is bovine serum albumin, ovalbumin, rabbit serum albumin, keyhole limpet hemocyanin, human gamma globulin, or multiple antigen peptide. Preferably, the carrier protein is conjugated to $X^2$ such as with an amide bond formation.

In another aspect, the present invention provides antibodies that specifically bind to a cyclic peptide as described herein. In some embodiments, the antibody is a monoclonal antibody. In some other embodiments, the antibody is a polyclonal antibody. In some embodiments, the antibody is a chimeric antibody. In some other embodiments, the antibody is a humanized antibody. In still other embodiments, the antibody is a therapeutic antibody.

In yet another aspect, the present invention provides methods of making antibodies that specifically bind to an exon 16-deleted HER2 ("HER2Δ16") polypeptide. In some embodiments, the method comprises:
 (a) providing a cyclic peptide as described herein;
 (b) administering the cyclic peptide to an animal under conditions supporting the production of antibodies; and
 (c) obtaining from the animal (i) an antibody that specifically binds to the HER2Δ16 polypeptide or (ii) a hybridoma that produces monoclonal antibodies which specifically bind to the HER2Δ16 polypeptide.

In still another aspect, the present invention provides a synthetic peptide having the formula as shown in FIG. 2, wherein $X^1$ is lysine, ornithine, β-amino-alanine, α,γ-diamino-butyric acid, or 2,7-diamino-heptanoic acid; and MPA is beta-mercaptopropionic acid. In some embodiments, $X^1$ is lysine.

In some embodiments, the synthetic peptide further comprises a carrier protein conjugated to the synthetic peptide. In some embodiments, the carrier protein is bovine serum albumin, ovalbumin, rabbit serum albumin, keyhole limpet hemocyanin, human gamma globulin, or multiple antigen peptide. Preferably, the carrier protein is conjugated to $X^1$ such as with an amide bond formation.

In yet another aspect, the present invention provides methods of making antibodies that specifically bind to a wild-type HER2 polypeptide. In some embodiments, the method comprises:
 (a) providing a synthetic peptide as described herein;
 (b) administering the synthetic peptide to an animal under conditions supporting the production of antibodies; and
 (c) obtaining from the animal (i) an antibody that specifically binds to the wild-type HER2 polypeptide or (ii) a hybridoma that produces monoclonal antibodies which specifically bind to the wild-type HER2 polypeptide.

These and other aspects, embodiments and objects will become more apparent when read with the detailed description and figures that follow.

BRIEF DESCRIPTION OF THE DRAWINGS

FIG. 2 shows HER2 synthetic peptide #1 for detecting wild-type HER2.

DETAILED DESCRIPTION OF THE INVENTION

I. Introduction

Figure 1:
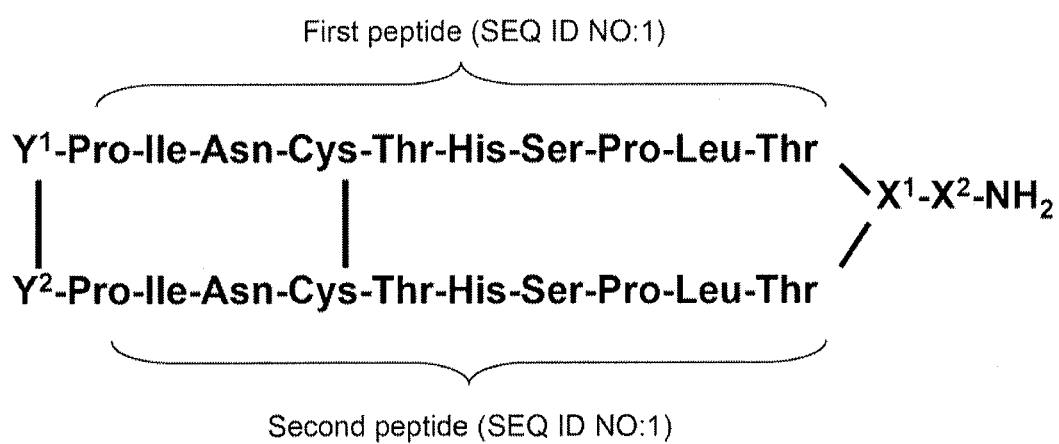
FIG. 1 shows a HER2Δ16 cyclic peptide with first and second peptides each having the amino acid sequence of SEQ ID NO:1.

The present invention is based in part on the discovery that while wild-type HER2 exists in cells in monomeric form, the HER2 splice variant HER2Delta16 ("HER2Δ16") forms a homodimer linked by disulfide bonds. This disulfide-linked dimer drives HER2Δ16 to an activated state and has been shown to activate multiple oncogenic signaling pathways in breast cancer tumor cells. Activation of oncogenic signaling pathways by HER2Δ16 leads to cell proliferation, motility, invasion, survival, and angiogenesis.

Accordingly, the present invention is drawn to cyclic peptides comprising a dimer of first and second peptides, each of the first and second peptides comprising a sequence corresponding to a portion of the HER2Δ16 polypeptide, wherein the cyclic peptides are cyclized via one or more disulfide bonds between the first and second peptides and via an amino acid residue linked to each of the first and second peptides. These peptides are useful for generating antibodies that specifically bind to HER2Δ16 homodimers.

II. Definitions

As used herein, the following terms have the meanings ascribed to them unless specified otherwise.

The term "HER2Delta16" or "HER2Δ16" refers to a variant of the human epidermal growth factor receptor 2 (HER2) gene in which exon 16 of the HER2 gene is absent.

The term "peptide" refers to a compound made up of a single chain of D- or L-amino acids or a mixture of D- and L-amino acids joined by peptide bonds. Generally, each of the peptides that form a dimer in the cyclic peptides of the present invention are about 2 to about 50 amino acids in length. Preferably, each of the peptides that form a dimer in the cyclic peptides of the present invention are each about 2 to about 25 amino acids in length, more preferably 3 to 20 amino acids in length, and most preferably 5 to 15 amino acids in length. Table 1 contains a preferred list of peptides useful in the present invention.

The term "amino acid" includes naturally-occurring α-amino acids and their stereoisomers, as well as unnatural amino acids and their stereoisomers. "Stereoisomers" of amino acids includes mirror image isomers of the amino acids, such as L-amino acids or D-amino acids. The naturally occurring amino acids are L-amino acids.

"Unnatural amino acids" include, but are not limited to, amino acid analogs, amino acid mimetics, and synthetic amino acids. Unnatural amino acids are not encoded by the genetic code and can, but do not necessarily have the same basic structure as a naturally occurring amino acid. Non-limiting examples of unnatural amino acids include azetidinecarboxylic acid, 2-aminoadipic acid, 3-aminoadipic acid, beta-amino-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, tertiary-butylglycine, 2,3-diamino-isobutyric acid, desmosine, 2,2'-diaminopimelic acid, 2,3-diaminopropionic acid, N-ethylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, ornithine, pentylglycine, pipecolic acid and thioproline.

Amino acids may be referred to herein by either their commonly known three letter symbols or by the one-letter symbols recommended by the IUPAC-IUB Biochemical Nomenclature Commission. For example, an L-amino acid may be represented herein by its commonly known three letter symbol (e.g., Arg for L-arginine) or by an upper-case one-letter amino acid symbol (e.g., R for L-arginine). A D-amino acid may be represented herein by its commonly known three letter symbol with "D" as prefix (e.g., DArg, D-Arg or dArg for D-arginine) or by a lower-case one-letter amino acid symbol (e.g., r for D-arginine).

With respect to amino acid sequences, one of skill in the art will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. The chemically similar amino acid includes, without limitation, a naturally-occurring amino acid such as an L-amino acid, a stereoisomer of a naturally occurring amino acid such as a D-amino acid, and an unnatural amino acid such as an amino acid analog, amino acid mimetic, synthetic amino acid, N-substituted glycine, and N-methyl amino acid.

Conservative substitution tables providing functionally similar amino acids are well known in the art. For example, substitutions may be made wherein an aliphatic amino acid (e.g., G, A, I, L, or V) is substituted with another member of the group. Similarly, an aliphatic polar-uncharged group such as C, S, T, M, N, or Q, may be substituted with another member of the group; and basic residues, e.g., K, R, or H, may be substituted for one another. In some embodiments, an amino acid with an acidic side chain, e.g., E or D, may be substituted with its uncharged counterpart, e.g., Q or N, respectively; or vice versa. Each of the following eight groups contains other exemplary amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

(see, e.g., Creighton, *Proteins*, 1984).

The terms "identical" or percent "identity," in the context of two or more nucleic acids or peptide sequences, refer to two or more sequences or subsequences that are the same or have a specified percentage of amino acid residues or nucleotides that are the same (i.e., at least about 70%, about 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection.

The term "disulfide bond-forming compound" refers to a compound that is able to form a disulfide bond (i.e., a covalent bond between two sulfur atoms) with another compound, which may or may not be an identical compound. Typically, a disulfide bond-forming compound contains a thiol group. In some embodiments, a disulfide bond-forming compound is a cysteine amino acid or beta-mercaptopropionic acid.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$ a dimer of Fab which itself is a light chain joined to $V_H$-$C_H$1 by a disulfide bond. The F(ab)'₂ may be reduced under mild conditions to break the disulfide linkage in the hinge region, thereby converting the F(ab)'₂ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. In some embodiments, the anti-HER2Δ16 antibodies of the present invention comprise humanized and/or chimeric monoclonal antibodies.

In one embodiment, the antibody is conjugated to an "effector" moiety. The effector moiety can be any number of molecules, including labeling moieties such as radioactive labels or fluorescent labels, or can be a therapeutic moiety. In one aspect the antibody modulates the activity of the protein. Such effector moieties include, but are not limited to, an anti-tumor drug, a toxin, a radioactive agent, a cytokine, a second antibody or an enzyme. Further, the invention provides an embodiment wherein the antibody of the invention is linked to an enzyme that converts a prodrug into a cytotoxic agent.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies can be selected to obtain only those polyclonal antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Using Antibodies, A Laboratory Manual* (1998) for a description of immunoassay formats and conditions that can be used to determine specific immunoreactivity).

The term "individual," "subject," or "patient" typically refers to humans, but also to other animals including, e.g., other primates, rodents, canines, felines, equines, ovines, porcines, and the like.

The term "therapeutically effective amount or dose" includes a dose of an agent (e.g., an anti-HER2Δ16 antibody) that is capable of achieving a therapeutic effect in a subject in need thereof. For example, a therapeutically effective amount of an anti-HER2Δ16 antibody can be the amount that is capable of preventing or relieving one or more symptoms associated with a HER2Δ16-overexpressing breast cancer. The exact amount can be ascertainable by one skilled in the art using known techniques (see, e.g., Lieberman, *Pharmaceutical Dosage Forms*, Vols. 1-3 (1992); Lloyd, *The Art, Science and Technology of Pharmaceutical Compounding* (1999); Pickar, *Dosage Calculations* (1999); and *Remington: The Science and Practice of Pharmacy*, 20th Edition, Gennaro, Ed., Lippincott, Williams & Wilkins (2003)).

III. HER2Delta16 Cyclic Peptides

In one aspect, the present invention provides a cyclic peptide comprising a dimer of a first peptide and a second peptide, wherein each of the first and second peptides comprise a sequence corresponding to a HER2Δ16 polypeptide. In some embodiments, the cyclic peptide is cyclized via (1) one or more disulfide bonds between the first peptide and the second peptide, and/or (2) an amino acid residue $X^1$ linked to an amino acid residue of the first peptide and an amino acid residue of the second peptide. In some embodiments, a disulfide bond between the first peptide and the second peptide is formed between a disulfide bond-forming compound $Y^1$ attached to the N-terminal end of the first peptide and a disulfide bond-forming compound $Y^2$ attached to the N-terminal end of the second peptide.

In preferred embodiments, the cyclic peptide comprises:
  a first peptide having an amino acid sequence corresponding to a HER2Δ16 polypeptide and a disulfide bond-forming compound $Y^1$ attached to the N-terminus of the first peptide; and
  a second peptide having an amino acid sequence corresponding to a HER2Δ16 polypeptide and a disulfide bond-forming compound $Y^2$ attached to the N-terminus of the second peptide;
wherein the cyclic peptide is cyclized via (1) a disulfide bond between $Y^1$ and $Y^2$, and (2) an amino acid residue $X^1$ linked to the C-terminus of the first peptide and to the C-terminus of the second peptide, as shown in FIG. 1.

A. HER2Δ16 Peptide Sequences

In some embodiments, each of the peptides of the cyclic peptide independently comprises an amino acid sequence that corresponds to a HER2Δ16 polypeptide. In some embodiments, each of the peptides of the cyclic peptide independently comprises an amino acid sequence that is substantially identical to (i.e., has at least about 70% identity, at least 75%, 80%, 85%, 90%, 91%, 92%, 93%, 94%, 95%, 96%, 97%, 98%, 99%, or higher amino acid sequence identity to) an amino acid sequence that spans exon 15 to exon 17 of a HER2Δ16 polypeptide. In some embodiments, each of the peptides of the cyclic peptide independently comprises an amino acid sequence that is substantially identical to (i.e., has at least about 70% identity, at least 75%, 80%, 85%, 90%, 91%, 92%, 93%, 94%, 95%, 96%, 97%, 98%, 99%, or higher amino acid sequence identity to) the amino acid sequence PINCTHSPLT (SEQ ID NO:1). In some embodiments, each of the peptides (i.e., the first peptide and the second peptide) of the cyclic peptide independently comprises the amino acid sequence of PINCTHSPLT (SEQ ID NO:1), or conservatively modified variants thereof.

In some embodiments, each of the first and second peptides has an amino acid sequence independently selected from the group consisting of the amino acid sequences listed in Table 1 below. In some embodiments, each of the first and second peptides has the same amino acid sequence (i.e., the sequence of the cyclic peptide is a palindromic sequence). In preferred embodiments, each of the first and second peptides has the amino acid sequence of SEQ ID NO:1.

TABLE 1

HER2A16 peptide and conservative substitutions thereof

| SEQ ID NO | Peptide sequence (N-terminal to C-terminal) |
|---|---|
| 1 | PINCTHSPLT |
| 2 | PLNCTHSPLT |
| 3 | PVNCTHSPLT |
| 4 | PINMTHSPLT |
| 5 | PINCSHSPLT |
| 6 | PINCTHTPLT |
| 7 | PINCTHSPIT |
| 8 | PINCTHSPVT |
| 9 | PINCTHSPLS |
| 10 | PLNMTHSPLT |
| 11 | PVNMTHSPLT |
| 12 | PLNCSHSPLT |
| 13 | PVNCSHSPLT |
| 14 | PLNCTHTPLT |
| 15 | PVNCTHTPLT |
| 16 | PLNCTHSPIT |
| 17 | PVNCTHSPIT |
| 18 | PLNCTHSPVT |
| 19 | PVNCTHSPVT |
| 20 | PLNCTHSPLS |
| 21 | PVNCTHSPLS |
| 22 | PINMSHSPLT |
| 23 | PINMTHTPLT |
| 24 | PINMTHSPIT |
| 25 | PINMTHSPVT |
| 26 | PINMTHSPLS |
| 27 | PINCSHTPLT |
| 28 | PINCSHSPIT |
| 29 | PINCSHSPVT |
| 30 | PINCSHSPLS |
| 31 | PINCTHTPIT |
| 32 | PINCTHTPVT |

TABLE 1-continued

HER2A16 peptide and conservative substitutions thereof

| SEQ ID NO | Peptide sequence (N-terminal to C-terminal) |
|---|---|
| 33 | PINCTHTPLS |
| 34 | PINCTHSPIS |
| 35 | PINCTHSPVS |
| 36 | PLNMSHSPLT |
| 37 | PVNMSHSPLT |
| 38 | PLNMTHTPLT |
| 39 | PVNMTHTPLT |
| 40 | PLNMTHSPIT |
| 41 | PLNMTHSPVT |
| 42 | PVNMTHSPIT |
| 43 | PVNMTHSPVT |
| 44 | PLNMTHSPLS |
| 45 | PVNMTHSPLS |
| 46 | PLNCSHTPLT |
| 47 | PVNCSHTPLT |
| 48 | PLNCSHSPIT |
| 49 | PLNCSHSPVT |
| 50 | PVNCSHSPIT |
| 51 | PVNCSHSPVT |
| 52 | PLNCSHSPLS |
| 53 | PVNCSHSPLS |
| 54 | PLNCTHTPIT |
| 55 | PLNCTHTPVT |
| 56 | PVNCTHTPIT |
| 57 | PVNCTHTPVT |
| 58 | PLNCTHSPIS |
| 59 | PLNCTHSPVS |
| 60 | PVNCTHSPIS |
| 61 | PVNCTHSPVS |
| 62 | CPINCTHSPLT |
| 63 | CPLNCTHSPLT |
| 64 | CPVNCTHSPLT |
| 65 | CPINMTHSPLT |
| 66 | CPINCSHSPLT |
| 67 | CPINCTHTPLT |
| 68 | CPINCTHSPIT |
| 69 | CPINCTHSPVT |

TABLE 1-continued

HER2A16 peptide and conservative substitutions thereof

| SEQ ID NO | Peptide sequence (N-terminal to C-terminal) |
|---|---|
| 70 | CPINCTHSPLS |
| 71 | CPLNMTHSPLT |
| 72 | CPVNMTHSPLT |
| 73 | CPLNCSHSPLT |
| 74 | CPVNCSHSPLT |
| 75 | CPLNCTHTPLT |
| 76 | CPVNCTHTPLT |
| 77 | CPLNCTHSPIT |
| 78 | CPVNCTHSPIT |
| 79 | CPLNCTHSPVT |
| 80 | CPVNCTHSPVT |
| 81 | CPLNCTHSPLS |
| 82 | CPVNCTHSPLS |
| 83 | CPINMSHSPLT |
| 84 | CPINMTHTPLT |
| 85 | CPINMTHSPIT |
| 86 | CPINMTHSPVT |
| 87 | CPINMTHSPLS |
| 88 | CPINCSHTPLT |
| 89 | CPINCSHSPIT |
| 90 | CPINCSHSPVT |
| 91 | CPINCSHSPLS |
| 92 | CPINCTHTPIT |
| 93 | CPINCTHTPVT |
| 94 | CPINCTHTPLS |
| 95 | CPINCTHSPIS |
| 96 | CPINCTHSPVS |
| 97 | CPLNMSHSPLT |
| 98 | CPVNMSHSPLT |
| 99 | CPLNMTHTPLT |
| 100 | CPVNMTHTPLT |
| 101 | CPLNMTHSPIT |
| 102 | CPLNMTHSPVT |
| 103 | CPVNMTHSPIT |
| 104 | CPVNMTHSPVT |
| 105 | CPLNMTHSPLS |
| 106 | CPVNMTHSPLS |
| 107 | CPLNCSHTPLT |
| 108 | CPVNCSHTPLT |
| 109 | CPLNCSHSPIT |
| 110 | CPLNCSHSPVT |
| 111 | CPVNCSHSPIT |
| 112 | CPVNCSHSPVT |
| 113 | CPLNCSHSPLS |
| 114 | CPVNCSHSPLS |
| 115 | CPLNCTHTPIT |
| 116 | CPLNCTHTPVT |
| 117 | CPVNCTHTPIT |
| 118 | CPVNCTHTPVT |
| 119 | CPLNCTHSPIS |
| 120 | CPLNCTHSPVS |
| 121 | CPVNCTHSPIS |
| 122 | CPVNCTHSPVS |
| 123 | PINCTHSPLTS |
| 124 | PLNCTHSPLTS |
| 125 | PVNCTHSPLTS |
| 126 | PINMTHSPLTS |
| 127 | PINCSHSPLTS |
| 128 | PINCTHTPLTS |
| 129 | PINCTHSPITS |
| 130 | PINCTHSPVTS |
| 131 | PINCTHSPLSS |
| 132 | PLNMTHSPLTS |
| 133 | PVNMTHSPLTS |
| 134 | PLNCSHSPLTS |
| 135 | PVNCSHSPLTS |
| 136 | PLNCTHTPLTS |
| 137 | PVNCTHTPLTS |
| 138 | PLNCTHSPITS |
| 139 | PVNCTHSPITS |
| 140 | PLNCTHSPVTS |
| 141 | PVNCTHSPVTS |
| 142 | PLNCTHSPLSS |
| 143 | PVNCTHSPLSS |

TABLE 1-continued

HER2A16 peptide and conservative substitutions thereof

| SEQ ID NO | Peptide sequence (N-terminal to C-terminal) |
|---|---|
| 144 | PINMSHSPLTS |
| 145 | PINMTHTPLTS |
| 146 | PINMTHSPITS |
| 147 | PINMTHSPVTS |
| 148 | PINMTHSPLSS |
| 149 | PINCSHTPLTS |
| 150 | PINCSHSPITS |
| 151 | PINCSHSPVTS |
| 152 | PINCSHSPLSS |
| 153 | PINCTHTPITS |
| 154 | PINCTHTPVTS |
| 155 | PINCTHTPLSS |
| 156 | PINCTHSPISS |
| 157 | PINCTHSPVSS |
| 158 | PLNMSHSPLTS |
| 159 | PVNMSHSPLTS |
| 160 | PLNMTHTPLTS |
| 161 | PVNMTHTPLTS |
| 162 | PLNMTHSPITS |
| 163 | PLNMTHSPVTS |
| 164 | PVNMTHSPITS |
| 165 | PVNMTHSPVTS |
| 166 | PLNMTHSPLSS |
| 167 | PVNMTHSPLSS |
| 168 | PLNCSHTPLTS |
| 169 | PVNCSHTPLTS |
| 170 | PLNCSHSPITS |
| 171 | PLNCSHSPVTS |
| 172 | PVNCSHSPITS |
| 173 | PVNCSHSPVTS |
| 174 | PLNCSHSPLSS |
| 175 | PVNCSHSPLSS |
| 176 | PLNCTHTPITS |
| 177 | PLNCTHTPVTS |
| 178 | PVNCTHTPITS |
| 179 | PVNCTHTPVTS |
| 180 | PLNCTHSPISS |
| 181 | PLNCTHSPVSS |
| 182 | PVNCTHSPISS |
| 183 | PVNCTHSPVSS |
| 184 | CPINCTHSPLTS |
| 185 | CPLNCTHSPLTS |
| 186 | CPVNCTHSPLTS |
| 187 | CPINMTHSPLTS |
| 188 | CPINCSHSPLTS |
| 189 | CPINCTHTPLTS |
| 190 | CPINCTHSPITS |
| 191 | CPINCTHSPVTS |
| 192 | CPINCTHSPLSS |
| 193 | CPLNMTHSPLTS |
| 194 | CPVNMTHSPLTS |
| 195 | CPLNCSHSPLTS |
| 196 | CPVNCSHSPLTS |
| 197 | CPLNCTHTPLTS |
| 198 | CPVNCTHTPLTS |
| 199 | CPLNCTHSPITS |
| 200 | CPVNCTHSPITS |
| 201 | CPLNCTHSPVTS |
| 202 | CPVNCTHSPVTS |
| 203 | CPLNCTHSPLSS |
| 204 | CPVNCTHSPLSS |
| 205 | CPINMSHSPLTS |
| 206 | CPINMTHTPLTS |
| 207 | CPINMTHSPITS |
| 208 | CPINMTHSPVTS |
| 209 | CPINMTHSPLSS |
| 210 | CPINCSHTPLTS |
| 211 | CPINCSHSPITS |
| 212 | CPINCSHSPVTS |
| 213 | CPINCSHSPLSS |
| 214 | CPINCTHTPITS |
| 215 | CPINCTHTPVTS |
| 216 | CPINCTHTPLSS |
| 217 | CPINCTHSPISS |

TABLE 1-continued

HER2Δ16 peptide and conservative substitutions thereof

| SEQ ID NO | Peptide sequence (N-terminal to C-terminal) |
|---|---|
| 218 | CPINCTHSPVSS |
| 219 | CPLNMSHSPLTS |
| 220 | CPVNMSHSPLTS |
| 221 | CPLNMTHTPLTS |
| 222 | CPVNMTHTPLTS |
| 223 | CPLNMTHSPITS |
| 224 | CPLNMTHSPVTS |
| 225 | CPVNMTHSPITS |
| 226 | CPVNMTHSPVTS |
| 227 | CPLNMTHSPLSS |
| 228 | CPVNMTHSPLSS |
| 229 | CPLNCSHTPLTS |
| 230 | CPVNCSHTPLTS |
| 231 | CPLNCSHSPITS |
| 232 | CPLNCSHSPVTS |
| 233 | CPVNCSHSPITS |
| 234 | CPVNCSHSPVTS |
| 235 | CPLNCSHSPLSS |
| 236 | CPVNCSHSPLSS |
| 237 | CPLNCTHTPITS |
| 238 | CPLNCTHTPVTS |
| 239 | CPVNCTHTPITS |
| 240 | CPVNCTHTPVTS |
| 241 | CPLNCTHSPISS |
| 242 | CPLNCTHSPVSS |
| 243 | CPVNCTHSPISS |
| 244 | CPVNCTHSPVSS |

Each of the first and second peptides of the cyclic peptide can independently comprise from about 7 to about 30 amino acid residues. In some embodiments, each of the first and second peptides of the cyclic peptide independently comprises from about 8 to about 25 amino acid residues, from about 9 to about 20 amino acid residues, or from about 10 to about 15 amino acid residues. In some embodiments, each of the first and second peptides of the cyclic peptide independently comprises 7, 8, 9, 10, 11, 12, 13, 14, 15, 16, 17, 18, 19, 20, 21, 22, 23, 24, 25, 26, 27, 28, 29, or 30 amino acid residues.

B. Cyclization of the Cyclic Peptide

In a preferred aspect, the HER2Δ16 cyclic peptides of the present invention are cyclized via disulfide bonds between an amino acid of the first peptide and an amino acid of the second peptide of the cyclic peptide and via the presence of an amino acid residue $X^1$ joined to both the first peptide and the second peptide. For ease of synthesis, $X^1$ and $X^2$ can optionally be appended to the first peptide. Cyclization of the cyclic peptide is shown in FIG. 1. As shown in FIG. 1, SEQ ID NO:1 is the first peptide as well as the second peptide. Any of the 244 sequences in Table 1 can be inserted into the first peptide and/or second peptide position. Preferably the same sequence is inserted into both the first peptide and second peptide positions (e.g., SEQ ID NO:1 for the first peptide and SEQ ID NO:1 for the second peptide). The cyclic peptide is preferably palindromic.

In some embodiments, each of the first and second peptides of the cyclic peptide comprises a disulfide bond-forming compound attached to a terminal end of each of the first and second peptides. The disulfide bond-forming compound may be attached to either the N-terminus of each of the first and second peptides, or to the C-terminus of each of the first and second peptides. In some embodiments, the HER2Δ16 cyclic peptides of the present invention are cyclized via disulfide bonds formed between disulfide bond-forming compound attached to the N-terminus of each of the first and second peptides.

In some embodiments, the disulfide bond-forming compound that is attached to the N-terminal end of each of the first and second peptides is a cysteine residue. In some embodiments, the disulfide bond-forming compound that is attached to the N-terminal end of each of the first and second peptides is beta-mercaptopropionic acid (βMPA in FIG. 1).

Alternatively or additionally, the HER2Δ16 cyclic peptides of the present invention are cyclized via disulfide bonds between the first peptide and the second peptide at residues other than a terminal residue. As a non-limiting example, in a cyclic peptide wherein each of the first and second peptides of the cyclic peptide independently comprises the amino acid sequence of PIN<u>C</u>THSPLT, the cyclic peptide can be cyclized via a disulfide bond between the cysteine residue of the first peptide and the cysteine residue of the second peptide (FIG. 1).

In some embodiments, the HER2Δ16 cyclic peptides of the present invention are cyclized via an amino acid residue $X^1$ that is linked to both the first peptide and the second peptide. $X^1$ may be attached to a terminal end (e.g., the C-terminus) of each of the first and/or second peptides. In some embodiments, the HER2Δ16 cyclic peptides of the present invention are cyclized via an $X^1$ that is attached to the C-terminus of each of the first and second peptides. $X^1$ may comprise a natural amino acid (i.e., an amino acid coded for by nucleic acid) or an unnatural amino acid. In some embodiments, $X^1$ comprises the amino acid lysine. In some embodiments, $X^1$ comprises an ornithine amino acid. In some embodiments, $X^1$ comprises a β-amino-alanine amino acid. In some embodiments, $X^1$ comprises an alpha, omega-diamino alkanoic acid (e.g., α,γ-diamino-butyric acid or 2,7-diamino-heptanoic acid). In some embodiments, the $X^1$ residue that is attached to the C-terminus of the first and/or second peptide has a free carboxylic acid (—COOH) at the C-terminus. In some embodiments, the $X^1$ residue that is attached to the C-terminus of the first and/or second peptide has an amidated C-terminus (—C(=O)—NH$_2$). In some embodiments, the $X^1$ residue that is attached to the C-terminus of the first and/or second peptide is affixed to a resin or attached to a carrier protein via the C-terminus ((—C(=O)-resin) or (—C(=O)-carrier protein)).

In some embodiments, the cyclic peptides of the invention further comprise an amino acid $X^2$ linked to the $X^1$ (FIG. 1). In some embodiments, wherein $X^1$ is attached to the C-terminus of each of the first and second peptides, $X^2$ is attached to the C-terminus of $X^1$. $X^2$ may comprise a natural amino acid or an unnatural amino acid. In some embodiments, $X^2$ comprises the amino acid lysine. In some embodiments, $X^2$ comprises an ornithine amino acid. In some embodiments, $X^2$ comprises a β-amino-alanine amino acid. In some embodiments, $X^2$ comprises an alpha, omega-diamino alkanoic acid (e.g., α,γ-diamino-butyric acid or 2,7-diamino-heptanoic acid). Preferably, a carrier protein as described herein is attached to $X^2$. In some embodiments, the $X^2$ residue that is attached to $X^1$ at the C-terminus of the first and/or second peptide has a free carboxylic acid (—COOH) at the C-terminus. In some embodiments, the $X^2$ residue has an amidated C-terminus (—C(=O)—NH$_2$). In some embodiments, the $X^1$ residue is affixed to a resin or attached to a carrier protein via the C-terminus ((—C(=O)-resin) or (—C(=O)-carrier protein)).

In preferred embodiments, the entire dimer of the first peptide and the second peptide is cyclized (i.e., the N-terminal residues of the first and second peptides are linked, e.g., via a disulfide bond, and the C-terminal residues of the first and second peptides are linked, e.g., via an amino acid $X^1$ that is linked to both the first peptide and the second peptide), as shown in FIG. 1.

The cyclized portion of the cyclic peptide can comprise from about 12 to about 50 amino acid residues including the first and second peptides. In some embodiments, the cyclized portion of the cyclic peptide comprises from about 13 to about 40 amino acid residues, from about 14 to about 35 amino acid residues, from about 15 to about 30 amino acid residues, from about 18 to about 28 amino acid residues, or from about 20 to about 25 amino acid residues. In some embodiments, the cyclized portion of the cyclic peptide comprises 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acid residues.

C. Carrier Proteins

In some embodiments, the HER2Δ16 cyclic peptides of the present invention further comprise one or more carrier proteins conjugated to the cyclic peptide. Conjugation of a carrier protein to a HER2Δ16 cyclic peptide is useful for generating a stronger immune response than would be otherwise generated by the HER2Δ16 cyclic peptide in the absence of the carrier protein.

Suitable carrier proteins for conjugation to peptides for generating antibodies are known in the art. In some embodiments, the carrier protein is bovine serum albumin, ovalbumin, rabbit serum albumin, keyhole limpet hemocyanin, bovine thyroglobulin, or soybean trypsin inhibitor, human gamma globulin, or multiple antigen peptide, or fragments thereof.

Carrier proteins may be conjugated to peptides either directly (i.e., without a linker molecule between the HER2Δ16 cyclic peptide and the carrier protein) or indirectly (i.e., with the aid of at least one linker molecule between the HER2Δ16 cyclic peptide and the carrier protein). Linker molecules useful in the present invention includes those possessing one or more different reactive functional groups that allow for covalent attachment of moieties such as a peptide to a carrier protein. In some embodiments, the linker molecule possesses two or more different reactive functional groups. In some cases multivalent linkers can be used and multiple cyclic peptides of the invention and/or carrier proteins can be linked via the linker. In some embodiments, the linker molecule is a bifunctional or derivatizing agent. Non-limiting examples of bifunctional or derivatizing agents include maleimidobenzoyl sulfosuccinimide ester (conjugation through cysteine residues), N-hydroxysuccinimide (conjugation through lysine residues), glutaraldehyde, succinic anhydride, SOCl$_2$, and R$_1$N=C=NR, wherein R and R$_1$ are different alkyl groups. Suitable linkers include, without limitation, those available from Pierce Biotechnology, Inc. (Rockford, Ill.). Carrier proteins and kits for conjugating carrier proteins to peptides are also readily commercially available, see, e.g., Thermo Scientific (Rockford, Ill.).

IV. Methods of Making Cyclic Peptides

In another aspect, the present invention provides methods of making HER2Δ16 cyclic peptides. In some embodiments, the HER2Δ16 cyclic peptides of the present invention can be produced by classical chemical synthesis, e.g., using solid phase techniques and/or automated peptide synthesizers.

Methods of synthesizing peptides using solid phase (e.g., Fmoc or t-Boc) or liquid phase synthesis techniques are generally known in the art. See, e.g., Chan & White, Eds., Fmoc Solid Phase Peptide Synthesis: A Practical Approach (Oxford University Press, 2000); Benoiton, Chemistry of Peptide Synthesis (CRC Press, 2005); Howl, Peptide Synthesis and Applications (Humana Press, 2010). In certain instances, peptides may be synthesized using solid phase strategies on an automated multiple peptide synthesizer (Abimed AMS 422) using 9-fluorenylmethyloxycarbonyl (Fmoc) chemistry. The synthesized peptides can then be isolated and/or purified by reversed phase-HPLC and lyophilized. Peptides may also be prepared according to the solid phase methods described by Atherton and Shepard, in "Solid phase peptide synthesis," IRL Press, Oxford, UK (1989). Peptide synthesis may alternatively be carried out in homogeneous solution. For example, the synthesis technique in homogeneous solution described by Houbenweyl, in "Methode der Organischen Chemie," edited by E. Wunsch, vol. 15-1 et 11, Thieme, Stuttgart, Germany (1974), can be used.

Methods of cyclizing peptides are also generally known in the art, e.g., the formation of thioethers and carboxyl- and amino-terminal amides and esters. In some embodiments, the HER2Δ16 cyclic peptides of the present invention are cyclized via disulfide bonds between a first HER2Δ16 peptide and a second HER2Δ16 peptide. In some embodiments, the HER2Δ16 cyclic peptides of the present invention are cyclized via one or more disulfide bonds between a cysteine residue of the first HER2Δ16 peptide and a cysteine residue of the second HER2Δ16 peptide. In some embodiments, the HER2Δ16 cyclic peptides of the present invention are cyclized via disulfide bonds between a beta-mercaptopropionic acid of the first HER2Δ16 peptide and a beta-mercaptopropionic acid of the second HER2Δ16 peptide. Disulfide bond formation can be accomplished, e.g., by air oxidation in the presence of an oxidizing agent such as DMSO or glutathione.

V. Antibodies to HER2Delta16 Cyclic Peptides

In another aspect, the present invention provides antibodies that specifically bind to a HER2Δ16 peptide or protein. In some embodiments, the antibody specifically binds to the region of exon 15 to exon 17 of HER2Δ16. In some embodiments, the antibody specifically binds to a homodimer of HER2Δ16.

A. Generation of Antibodies

Antibodies that specifically bind to a HER2Δ16 peptide or protein can be generated using any of the HER2Δ16 cyclic peptides as described herein (e.g., a HER2Δ16 cyclic peptide conjugated to a carrier protein). A synthesized HER2Δ16 cyclic peptide of the present invention can be administered to an animal, for example mice or rabbits, to generate polyclonal or monoclonal antibodies. One skilled in the art will recognize that many procedures are available for the production of antibodies, for example, as described in *Antibodies, A Laboratory Manual*, Harlow and Lane, Eds., Cold Spring Harbor Laboratory, Cold Spring Harbor, N.Y. (1988).

Polyclonal antibodies can be raised in animals by multiple subcutaneous (sc) or intraperitoneal (ip) injections of a HER2Δ16 cyclic peptide and an adjuvant. Animals are immunized against the HER2Δ16 cyclic peptide or an immunogenic conjugate thereof by combining, e.g., 100 μg (for rabbits) or 5 μg (for mice) of the antigen or conjugate with 3 volumes of Freund's complete adjuvant and injecting the solution intradermally at multiple sites. One month later, the animals are boosted with about ⅕ to ⅒ the original amount of HER2Δ16 cyclic peptide or conjugate in Freund's incomplete adjuvant by subcutaneous injection at multiple sites. Seven to fourteen days later, the animals are bled and the serum is assayed for antibody titer. Animals are typically boosted until the titer plateaus. Preferably, the animal is boosted with the conjugate of the same HER2Δ16 cyclic peptide, but a conjugate of a different HER2Δ16 cyclic peptide may also be used.

Monoclonal antibodies are generally obtained from a population of substantially homogeneous antibodies, i.e., the individual antibodies comprising the population are identical except for possible naturally-occurring mutations that may be present in minor amounts. Thus, the modifier "monoclonal" indicates the character of the antibody as not being a mixture of discrete antibodies. For example, monoclonal antibodies can be made using the hybridoma method described by Kohler et al., *Nature*, 256:495 (1975) or by any recombinant DNA method known in the art (see, e.g., U.S. Pat. No. 4,816,567).

In the hybridoma method, a mouse or other appropriate host animal (e.g., hamster) is immunized as described above to elicit lymphocytes that produce or are capable of producing antibodies which specifically bind to the HER2Δ16 cyclic peptide used for immunization. Alternatively, lymphocytes are immunized in vitro. The immunized lymphocytes are then fused with myeloma cells using a suitable fusing agent, such as polyethylene glycol, to form hybridoma cells (see, e.g., Goding, *Monoclonal Antibodies: Principles and Practice*, Academic Press, pp. 59-103 (1986)). The hybridoma cells thus prepared are seeded and grown in a suitable culture medium that preferably contains one or more substances which inhibit the growth or survival of the unfused, parental myeloma cells.

Preferred myeloma cells are those that fuse efficiently, support stable high-level production of antibody by the selected antibody-producing cells, and/or are sensitive to a medium such as HAT medium. Examples of such preferred myeloma cell lines for the production of human monoclonal antibodies include, but are not limited to, murine myeloma lines such as those derived from MOPC-21 and MPC-11 mouse tumors (available from the Salk Institute Cell Distribution Center; San Diego, Calif.), SP-2 or X63-Ag8-653 cells (available from the American Type Culture Collection; Rockville, Md.), and human myeloma or mouse-human heteromyeloma cell lines (see, e.g., Kozbor, *J. Immunol.*, 133:3001 (1984); and Brodeur et al., *Monoclonal Antibody Production Techniques and Applications*, Marcel Dekker, Inc., New York, pp. 51-63 (1987)).

The culture medium in which hybridoma cells are grown can be assayed for the production of monoclonal antibodies directed against the HER2Δ16 cyclic peptide of interest. The binding specificity of monoclonal antibodies produced by hybridoma cells can be determined by immunoprecipitation or by an in vitro binding assay, such as a radioimmunoassay (RIA) or an enzyme-linked immunoabsorbent assay (ELISA). The binding affinity of monoclonal antibodies can be determined using, e.g., the Scatchard analysis of Munson et al., *Anal. Biochem.*, 107:220 (1980).

The production of monoclonal antibodies is well known in the art. In general, spleen cells from an animal immunized with a HER2Δ16 cyclic peptide as described herein are immortalized, commonly by fusion with a myeloma cell (see, Kohler & Milstein, *Eur. J. Immunol.* 6:511-519 (1976). Colonies arising from single immortalized cells are screened for the production of antibodies having the desired binding specificity and binding affinity for the particular antigen. In some embodiments, the immunized animal is a transgenic animal that expresses human immunoglobulin genes for the production of human antibodies, as disclosed in U.S. Pat. No. 6,833,268. In some embodiments, the production of human or humanized antibodies is carried out as described in U.S. Pat. No. 6,673,986, or using methods known to a person of ordinary skill in the art.

After hybridoma cells are identified that produce anti-HER2Δ16 antibodies of the desired specificity, affinity, and/or activity, the clones may be subcloned by limiting dilution procedures and grown by standard methods (see, e.g., Goding, *Monoclonal Antibodies: Principles and Practice*, Academic Press, pp. 59-103 (1986)). Suitable culture media for this purpose include, for example, D-MEM or RPMI-1640 medium. In addition, the hybridoma cells may be grown in vivo as ascites tumors in an animal. The monoclonal antibodies secreted by the subclones can be separated from the culture medium, ascites fluid, or serum by conventional antibody purification procedures such as, for example, protein A-Sepharose, hydroxylapatite chromatography, gel electrophoresis, dialysis, or affinity chromatography.

The monoclonal anti-HER2Δ16 peptide antibody (e.g., a mouse monoclonal antibody) can be chimerized by substituting the mouse constant regions of the antibody with that from human antibodies by standard recombinant DNA and molecular biology techniques. The desirable chimeric antibody is one that retains the antigen specificity and affinity of its parental mouse monoclonal antibody.

In certain embodiments, the variable regions of the heavy-chain and light-chain of the parental monoclonal antibody are isolated by RT-PCR from hybridoma cells and ligated in-frame to human IgG1 heavy-chain and kappa light chain constant regions, respectively, in mammalian expression vectors. Alternatively a human Ig expression vector such as TCAE 5.3 can be used. The expression vector contains the human IgG1 heavy-chain and kappa light-chain constant region genes on the same plasmid (Preston et al., *Infection & Immunity* 66:4137-42, (1998)). Expression vectors encoding chimeric heavy- and light-chains can then be co-transfected into an appropriate mammalian cell line for chimeric antibody production. Immunoreactivity and affinity of chimeric antibodies are compared to parental murine antibodies by ELISA and FACS.

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can include rational and empirical methods. Rational methods consist of generating a small set of variants, which are designed based on the antibody structure and/or amino acid sequence, and assessing the binding and biological properties of the variants (see, e.g., Almagro et al., Frontiers in Bioscience, 13: 1619-1633 (2008)). Examples of rational methods include CDR grafting, resurfacing, superhumanization, and human string content optimization. Empirical methods are based on generating large combinatorial libraries and selecting for the desired variants through enrichment approaches or high-through put screening techniques. Examples of empirical methods include framework libraries, guided selection, framework shuffling and humaneering.

In some embodiments, humanization can be essentially performed following the method of Winter and co-workers (see, e.g., Jones et al., Nature 321:522-525 (1986); Riechmann et al., Nature 332:323-327 (1988); Verhoeyen et al., Science 239:1534-1536 (1988) and Presta, Curr. Op. Struct. Biol. 2:593-596 (1992)), by substituting non-human CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some framework residues are substituted by residues from analogous sites in rodent antibodies.

The choice of human variable domains, both light and heavy, to be used in making the humanized antibodies described herein is an important consideration for reducing antigenicity. According to the so-called "best-fit" method, the sequence of the variable domain of a rodent antibody is screened against the entire library of known human variable-domain sequences. The human sequence which is closest to that of the rodent is then accepted as the human framework for the humanized antibody (see, e.g., Sims et al., J. Immunol., 151:2296 (1993); and Chothia et al., J. Mol. Biol., 196:901 (1987)). Another method uses a particular framework derived from the consensus sequence of all human antibodies of a particular subgroup of light or heavy chains. The same framework may be used for several different humanized antibodies (see, e.g., Carter et al., Proc. Natl. Acad. Sci. USA, 89:4285 (1992); and Presta et al., J. Immunol., 151:2623 (1993)).

Computer-generated three-dimensional modeling of V domains can be used to humanize the V regions and key residues of the mouse framework that maintain the structure of the CDRs and the integrity of the antigen-binding site. Briefly, three-dimensional modeling of the V regions can be performed using software such as ABMOD, ENCAD, AMBER, 3D-JIG-SAW and SWISS-MODEL. The human frameworks can be selected using the Kabat database to obtain human V region sequences from mouse VH and VL sequences, and then using the Smith-Waterman or BLAST algorithms to identify human sequences with high homology to the mouse sequence. Next, the key mouse framework residues that potentially influence the conformation of the antigen-binding site or directly interact with the antigen are identified using computer software programs such as RASMOL. The impact of replacing the mouse residue with its human counterpart should be analyzed and determined for each key framework residue. In some instances, if the amino acid at a key framework position differs between the mouse and human sequences, the humanized form of the antibody can contain the mouse variant if it preserves the CDR structure. When, creating a humanized antibody, consideration is given to maintaining the affinity and specificity of the parental monoclonal antibody.

As an alternative to humanization, human antibodies can be generated. As a non-limiting example, transgenic animals (e.g., mice) can be produced that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggermann et al., Year in Immun., 7:33 (1993); and U.S. Pat. Nos. 5,591,669, 5,589,369, and 5,545,807.

In some embodiments, antibody fragments are generated. Various techniques have been developed for the production of antibody fragments. Traditionally, these fragments were derived via proteolytic digestion of intact antibodies (see, e.g., Morimoto et al., J. Biochem. Biophys. Meth., 24:107-117 (1992); and Brennan et al., Science, 229:81 (1985)). However, these fragments can now be produced directly using recombinant host cells. For example, antibody fragments can be isolated from antibody phage libraries. Alternatively, Fab'-SH fragments can be directly recovered from E. coli cells and chemically coupled to form F(ab')$_2$ fragments (see, e.g., Carter et al., BioTechnology, 10:163-167 (1992)). According to another approach, F(ab')$_2$ fragments can be isolated directly from recombinant host cell culture. Other techniques for the production of antibody fragments will be apparent to those skilled in the art. In other embodiments, the antibody of choice is a single chain Fv fragment (scFv). See, e.g., PCT Publication No. WO 93/16185; and U.S. Pat. Nos. 5,571,894 and 5,587,458. The antibody fragment may also be a linear antibody as described, e.g., in U.S. Pat. No. 5,641,870.

B. Diagnostic Antibodies

In some embodiments, antibodies that specifically bind to a HER2Δ16 peptide or protein find use as diagnostic agents. Diagnostic anti-HER2Δ16 antibodies of the present invention can be used to determine whether and to what extent the HER2Δ16 splice variant is expressed in a sample of interest, e.g., a sample associated with breast cancer.

Diagnostic assays using anti-HER2Δ16 antibodies to detect HER2Δ16 in a sample of interest include any quantitative or qualitative assay known to one of skill in the art. In certain instances, anti-HER2Δ16 antibodies can be used in qualitative assays that determine the presence or absence of HER2Δ16 homodimers in a sample of interest. In certain other instances, anti-HER2Δ16 antibodies can be used in quantitative assays that determine the relative or absolute amount of HER2Δ16 homodimers in a sample of interest. One skilled in the art will appreciate that any assay useful for determining the level of HER2Δ16 expression is also useful for determining the presence or absence of HER2Δ16 expression.

A variety of immunoassay techniques, including competitive and non-competitive immunoassays, can be used to determine the presence or level of HER2Δ16 expression in a sample (see, e.g., Self and Cook, Curr. Opin. Biotechnol., 7:60-65 (1996)). The term immunoassay encompasses techniques including, without limitation, enzyme immunoassays (EIA) such as enzyme multiplied immunoassay technique (EMIT), enzyme-linked immunosorbent assay (ELISA), antigen capture ELISA, sandwich ELISA, IgM antibody capture ELISA (MAC ELISA), and microparticle enzyme immunoassay (MEIA); capillary electrophoresis immunoassays (CEIA); radioimmunoassays (RIA); immunoradiometric assays (IRMA); fluorescence polarization immunoassays (FPIA); and chemiluminescence assays (CL). If desired, such immunoassays can be automated. Immunoassays can also be used in conjunction with laser induced fluorescence (see, e.g., Schmalzing and Nashabeh, *Electrophoresis*, 18:2184-2193 (1997); Bao, *J. Chromatogr. B. Biomed. Sci.*, 699:463-480 (1997)). Liposome immunoassays, such as flow-injection liposome immunoassays and liposome immunosensors, are also suitable for use in the present invention (see, e.g., Rongen et al., *J Immunol. Methods*, 204:105-133 (1997)). In addition, nephelometry assays, in which the formation of protein/antibody complexes results in increased light scatter that is converted to a peak rate signal as a function of the marker concentration, are suitable for use in the present invention. Nephelometry assays are commercially available from Beckman Coulter (Brea, Calif.; Kit #449430) and can be performed using a Behring Nephelometer Analyzer (Fink et al., *J Clin. Chem. Clin. Biol. Chem.*, 27:261-276 (1989)).

Antigen capture ELISA can be useful for determining the presence or level of HER2Δ16 expression in a sample. For example, in an antigen capture ELISA, an antibody directed to a marker of interest is bound to a solid phase and sample is added such that the marker is bound by the antibody. After unbound proteins are removed by washing, the amount of bound marker can be quantitated using, e.g., a radioimmunoassay (see, e.g., Harlow and Lan e, Antibodies: A Laboratory Manual, Cold Spring Harbor Laboratory, New York, 1988)). Sandwich ELISA can also be suitable for use in the present invention. For example, in a two-antibody sandwich assay, a first antibody is bound to a solid support, and the marker of interest is allowed to bind to the first antibody. The amount of the marker is quantitated by measuring the amount of a second antibody that binds the marker. The antibodies can be immobilized onto a variety of solid supports, such as magnetic or chromatographic matrix particles, the surface of an assay plate (e.g., microtiter wells), pieces of a solid substrate material or membrane (e.g., plastic, nylon, paper), and the like. An assay strip can be prepared by coating the antibody or a plurality of antibodies in an array on a solid support. This strip can then be dipped into the test sample and processed quickly through washes and detection steps to generate a measurable signal, such as a colored spot.

A radioimmunoassay using, for example, an iodine-125 ($^{125}$I) labeled secondary antibody (Harlow and Lane, supra) is also suitable for determining the presence or level of HER2Δ16 expression in a sample. A secondary antibody labeled with a chemiluminescent marker can also be suitable for use in the present invention. A chemiluminescence assay using a chemiluminescent secondary antibody is suitable for sensitive, non-radioactive detection of marker levels. Such secondary antibodies can be obtained commercially from various sources, e.g., Amersham Lifesciences, Inc. (Arlington Heights, Ill.).

Specific immunological binding of the anti-HER2Δ16 antibody to HER2Δ16 homodimers can be detected directly or indirectly. Direct labels include fluorescent or luminescent tags, metals, dyes, radionuclides, and the like, attached to the antibody. An antibody labeled with iodine-125 ($^{125}$I) can be used for determining the levels of one or more markers in a sample. A chemiluminescence assay using a chemiluminescent antibody specific for the marker is suitable for sensitive, non-radioactive detection of marker levels. An antibody labeled with fluorochrome is also suitable for determining the levels of one or more markers in a sample. Examples of fluorochromes include, without limitation, DAPI, fluorescein, Hoechst 33258, R-phycocyanin, B-phycoerythrin, R-phycoerythrin, rhodamine, Texas red, and lissamine. Secondary antibodies linked to fluorochromes can be obtained commercially, e.g., goat F(ab')$_2$ anti-human IgG-FITC is available from Tago Immunologicals (Burlingame, Calif.).

Indirect labels include various enzymes well-known in the art, such as horseradish peroxidase (HRP), alkaline phosphatase (AP), β-galactosidase, urease, and the like. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-β-D-galactopyranoside (ONPG), which yields a soluble product detectable at 410 nm. An urease detection system can be used with a substrate such as urea-bromocresol purple (Sigma Immunochemicals; St. Louis, Mo.). A useful secondary antibody linked to an enzyme can be obtained from a number of commercial sources, e.g., goat F(ab')$_2$ anti-human IgG-alkaline phosphatase can be purchased from Jackson ImmunoResearch (West Grove, Pa.).

A signal from the direct or indirect label can be analyzed, for example, using a spectrophotometer to detect color from a chromogenic substrate; a radiation counter to detect radiation such as a gamma counter for detection of $^{125}$I; or a fluorometer to detect fluorescence in the presence of light of a certain wavelength. For detection of enzyme-linked antibodies, a quantitative analysis of the amount of marker levels can be made using a spectrophotometer such as an EMAX Microplate Reader (Molecular Devices; Menlo Park, Calif.) in accordance with the manufacturer's instructions. If desired, the assays of the present invention can be automated or performed robotically, and the signal from multiple samples can be detected simultaneously.

Quantitative Western blotting can also be used to detect or determine the presence or level of HER2Δ16 expression in a sample. Western blots can be quantitated by well-known methods such as scanning densitometry or phosphorimaging. As a non-limiting example, protein samples are electrophoresed on 10% SDS-PAGE Laemmli gels. Primary murine monoclonal antibodies are reacted with the blot, and antibody binding can be confirmed to be linear using a preliminary slot blot experiment. Goat anti-mouse horseradish peroxidase-coupled antibodies (BioRad) are used as the secondary antibody, and signal detection performed using chemiluminescence, for example, with the Renaissance chemiluminescence kit (New England Nuclear; Boston, Mass.) according to the manufacturer's instructions. Autoradiographs of the blots are analyzed using a scanning densitometer (Molecular Dynamics; Sunnyvale, Calif.) and normalized to a positive control. Values are reported, for example, as a ratio between the actual value to the positive control (densitometric index). Such methods are well known in the art as described, for example, in Parra et al., *J. Vasc. Surg.*, 28:669-675 (1998).

Alternatively, a variety of immunohistochemical assay techniques can be used to determine the presence or level of HER2Δ16 expression as one or more markers in a sample. The term immunohistochemical assay encompasses techniques that utilize the visual detection of fluorescent dyes or enzymes coupled (i.e., conjugated) to antibodies that react with the marker of interest using fluorescent microscopy or light microscopy and includes, without limitation, direct fluorescent antibody assay, indirect fluorescent antibody (IFA) assay, anticomplement immunofluorescence, avidin-biotin immunofluorescence, and immunoperoxidase assays. An IFA assay, for example, is useful for determining whether a sample is positive for ANCA, the level of ANCA in a sample, whether a sample is positive for pANCA, the level of pANCA in a sample, and/or an ANCA staining pattern (e.g., cANCA, pANCA, NSNA, and/or SAPPA staining pattern). The concentration of ANCA in a sample can be quantitated, e.g., through endpoint titration or through measuring the visual intensity of fluorescence compared to a known reference standard.

C. Therapeutic Antibodies

In some embodiments, antibodies that specifically bind to a HER2Δ16 peptide or protein find use as therapeutic agents. For therapeutic applications, a therapeutically effective amount of an anti-HER2Δ16 antibody can be administered to an individual in need thereof, e.g., a patient having a cancer (e.g., breast cancer) that overexpresses HER2Δ16. An anti-HER2Δ16 antibody can be administered alone or co-administered in combination with one or more additional therapeutic agents (e.g., chemotherapeutic agents for treating a cancer such as breast cancer).

Anti-HER2Δ16 antibody compositions for therapeutic use may be dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs.

The anti-HER2Δ16 antibody formulations can be administered in a variety of unit dosage forms depending upon the method of administration. For example, unit dosage forms suitable for oral administration include, but are not limited to, powder, tablets, pills, capsules and lozenges. Methods for preparing such dosage forms are known to those skilled in the art (see, e.g., *REMINGTON'S PHARMACEUTICAL SCIENCES*, 18TH ED., Mack Publishing Co., Easton, Pa. (1990)). It is recognized that antibodies when administered orally, should be protected from digestion. This is typically accomplished either by complexing the molecules with a composition to render them resistant to acidic and enzymatic hydrolysis, or by packaging the molecules in an appropriately resistant carrier, such as a liposome or a protection barrier. Means of protecting agents from digestion are well known in the art.

Pharmaceutical formulations of the antibodies for use with the present invention can be prepared by mixing an antibody having the desired degree of purity with optional pharmaceutically acceptable carriers, excipients or stabilizers. Such formulations can be lyophilized formulations or aqueous solutions. Acceptable carriers, excipients, or stabilizers are nontoxic to recipients at the dosages and concentrations used. Acceptable carriers, excipients or stabilizers can be acetate, phosphate, citrate, and other organic acids; antioxidants (e.g., ascorbic acid); preservatives; low molecular weight polypeptides; proteins, such as serum albumin or gelatin, or hydrophilic polymers such as polyvinylpyrrolidone; and amino acids, monosaccharides, disaccharides, and other carbohydrates including glucose, mannose, or dextrins; chelating agents; and ionic and non-ionic surfactants (e.g., polysorbate); salt-forming counter-ions such as sodium; metal complexes (e.g., Zn-protein complexes); and/or non-ionic surfactants. The antibody can be formulated at a concentration of between 0.5-200 mg/ml, or between 10-50 mg/ml.

In therapeutic use for the treatment of cancer, an anti-HER2Δ16 antibody can be administered at the initial dosage of from about 0.001 mg/kg to about 1000 mg/kg daily. A daily dose range of from about 0.01 mg/kg to about 500 mg/kg, from about 0.1 mg/kg to about 200 mg/kg, from about 1 mg/kg to about 100 mg/kg, or from about 10 mg/kg to about 50 mg/kg, can be used. The dosages, however, may be varied depending upon the requirements of the individual, the severity of the cancer, and the anti-HER2Δ16 antibody being employed. The dose administered to an individual, in the context of the present invention, should be sufficient to affect a beneficial therapeutic response in the individual over time. The size of the dose can also be determined by the existence, nature, and extent of any adverse side-effects that accompany the administration of a particular anti-HER2Δ16 antibody in an individual. Determination of the proper dosage for a particular situation is within the skill of the practitioner. Generally, treatment is initiated with smaller dosages which are less than the optimum dose of the anti-HER2Δ16 antibody. Thereafter, the dosage is increased by small increments until the optimum effect under circumstances is reached. For convenience, the total daily dosage may be divided and administered in portions during the day, if desired.

VI. Examples

The present invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

Example 1. Design and Synthesis of Synthetic Peptides for Raising Antibodies Against HER2Δ16

Peptides can be designed and synthesized for raising antibodies in order to develop therapies and assays for detecting the presence of HER2 or HER2Δ16 protein in a sample. These peptides span either the exons 15, 16, and 17 region of HER2 and mimic the monomeric structure of the wild-type HER2 for specific detection of HER2 or span only the exons 15 and 17 region of HER2 with exon 16 deleted and mimic the homodimeric structure of the HER2Δ16 protein for specific detection of HER2Δ16.

For detecting wild-type HER2, synthetic peptide #1 was designed to have the formula as shown in FIG. 2, wherein "MPA" is β-mercaptopropionic acid. See FIG. 2. Synthesis of synthetic peptide #1 was accomplished by solid-phase methodology using the 4-methylbenzhydrylamine resin and the di-isopropyl-carbodiimide (DIC) coupling procedure, followed by trifluoroacetic acid (TFA) deprotection of the t-butyloxycarbonyl-protecting (Boc) group on the $N^\alpha$-amino functional group of the coupled amino acid to grow the peptide chain. Amino acid side-chain functional group protections are as follows: benzyl (Bzl) for Glu, Asp, Thr, Ser, Cys and MPA; tosyl (Tos) for His and Arg; 2-chlorobenzyloxycarbonyl (ClZ) for Lys. These side-chain protecting groups are not removed during the TFA deprotection steps and thus protect the peptide-chain during its synthesis. Briefly, in order to start the synthesis, the 4-methylbenzhydrylamine resin (1) was washed with dichloromethane (DCM), neutralized with 10% diisopropylethylamine (DIEA)/DCM, and washed with methanol (MeOH). The first protected amino acid, Boc-Lys(ClZ)—OH (2), was added and coupled for 2 hours to the resin to form an amide bond with the 4-methylbenzhydrylamine, followed by DCM and MeOH washing. The $N^\alpha$-Boc-protected Lys(ClZ) coupled on the resin (3) was then deprotected with 45% TFA/DCM to expose its $N^\alpha$-amino functional group, followed by DCM and MeOH washing, DIEA/DCM neutralization, and DCM and MeOH washing. The second Boc-protected amino acid (Boc-Thr(Bzl)-OH) (4) was then added and coupled with DIC for 2 hours, followed by washing, acetic anhydride ($Ac_2O$) capping, and washing to generate a dipeptide on the solid support (5). Likewise, after deprotection, washing, neutralization and washing, the following $N^\alpha$-Boc-protected amino acids, in the order, Leu, Pro, Ser(Bzl), Ala, Arg(Tos), Gln, Glu(Bzl), Ala, Pro, Cys(Bzl), Gly, Lys(ClZ), Asp(Bzl), Asp(Bzl), Leu, Asp(Bzl), Val, Cys(Bzl), Ser(Bzl), His(Tos), Thr(Bzl), Cys(Bzl), Asn, Ile, Pro and MPA(Bzl) were, respectively, coupled to form the growing peptide chain. After the last amino acid was coupled, the protected peptide-resin was treated with hydrogen fluoride to cleave the peptide from the resin as well as to remove all the side-chain protecting groups from the peptide to yield the crude synthetic peptide #1 with an amidated carboxy-terminus. The two disulfide bonds in the crude peptide are then cyclized by air oxidation in reduced and oxidized glutathione to yield the final product, synthetic peptide #1.

For detecting HER2Δ16, synthetic peptide #2 is designed having the formula:

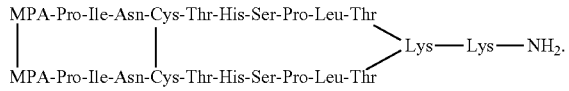

Figure 3:
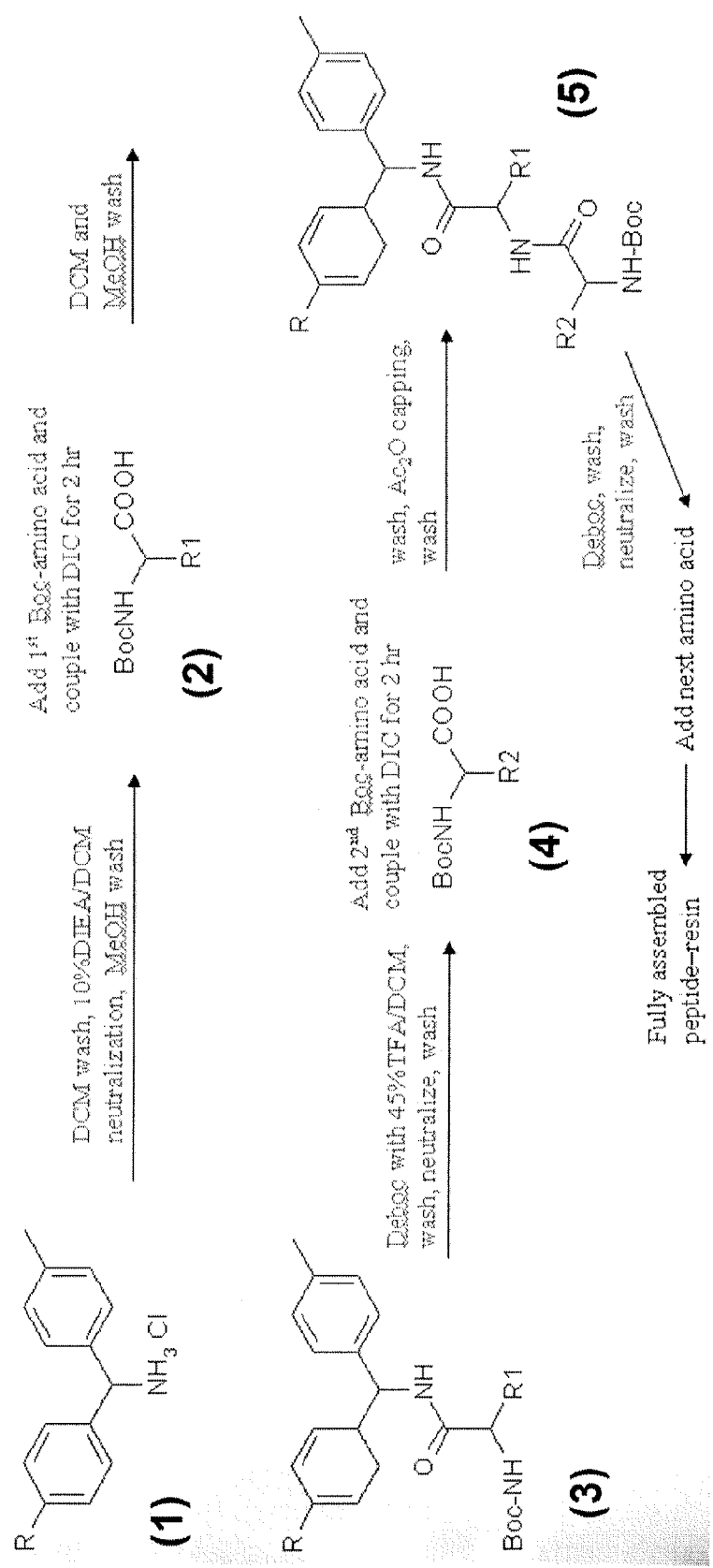
FIG. 3 shows the synthesis of a HER2 synthetic peptide #2.

Synthesis of synthetic peptide #2 (FIG. 3) was accomplished by a similar solid-phase methodology as used in the synthesis of synthetic peptide #1, except after the coupling of the first amino acid Boc-Lys(ClZ)—OH, the second lysine amino acid employed was Boc-Lys(Boc)-OH, which has a t-Boc protection on both the $N^\alpha$-amino group and the $N^\epsilon$-amino group of lysine, so that when it is deprotected with TFA, both amino functional groups are exposed and available for growing two identical peptide chains simultaneously during the rest of the synthesis. Thus, after deprotection, washing, neutralization and washing, the following $N^\alpha$-Boc-protected amino acids, in the order, Thr(Bzl), Leu, Pro, Ser(Bzl), His(Tos), Thr(Bzl), Cys(Bzl), Asn, Ile, Pro MPA(Bzl) were, respectively, coupled to form the two branched peptide chains. After the last amino acid was coupled, the protected peptide-resin is treated with hydrogen fluoride to cleave the peptide from the resin as well as to remove all the side-chain protecting groups from the branched peptide to yield the crude synthetic peptide #2 with an amidated carboxy-terminus. The two disulfide bonds in the crude peptide (a first disulfide bond between the MPA molecules and a second disulfide bond between the cysteine residues) were then cyclized by air oxidation in reduced and oxidized glutathione to yield the final product, synthetic peptide #2.

Example 2. Analysis of Synthetic Peptides for Raising Antibodies Against HER2Δ16

A synthetic peptide #1 having the formula shown in FIG. 2 and as described in Example 1, wherein "MPA" is β-mercaptopropionic acid, and a synthetic peptide #2 having the formula:

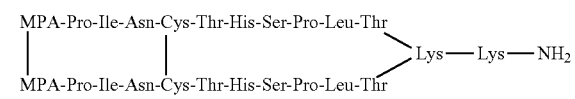

and as described in Example 1, were synthesized according to the methods described in Example 1. The synthesized peptides were then analyzed by high performance liquid chromatography (HPLC) and mass spectrometry as described below.

Samples comprising synthetic peptides #1 or #2 were subjected to reverse-phase HPLC on a C18 column. The samples were reconstituted in Solvent A, 0.1% trifluoroacetic acid (TFA) in water and applied to the column. The peptides were eluted from the column using Solvent B, 0.1% TFA in acetonitrile, at a gradient of 0% solvent B to 60% solvent B in 20 minutes. Detection of eluted peptides was performed at a wavelength of 220 nm. For peptide #1, the peak area percentage was calculated as ≥95%. For peptide #2, the peak area percentage was calculated as ≥90%.

Figure 4:
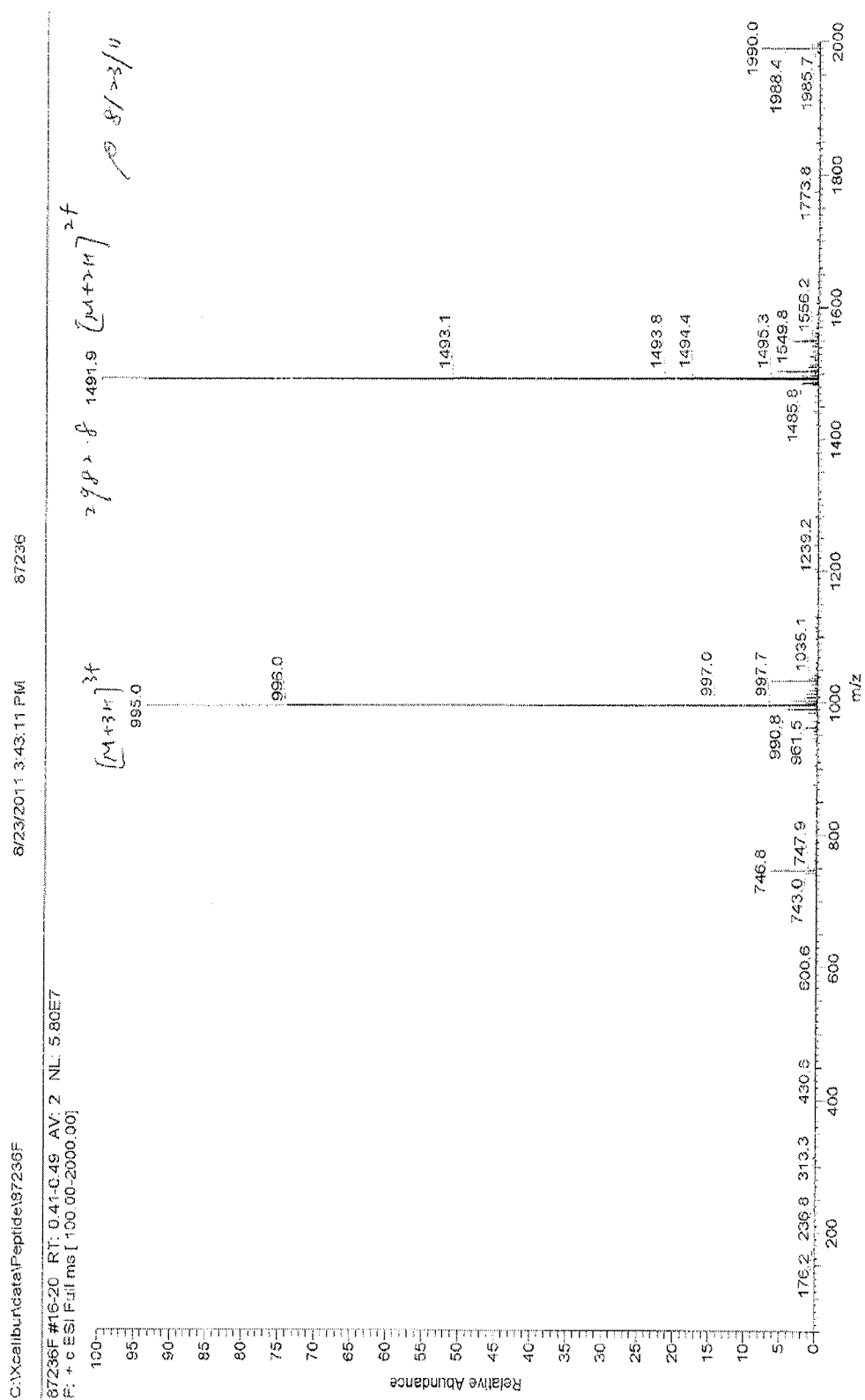
FIG. 4 shows mass spectrometry results for the synthesized HER2 synthetic peptide #1.
Figure 5:
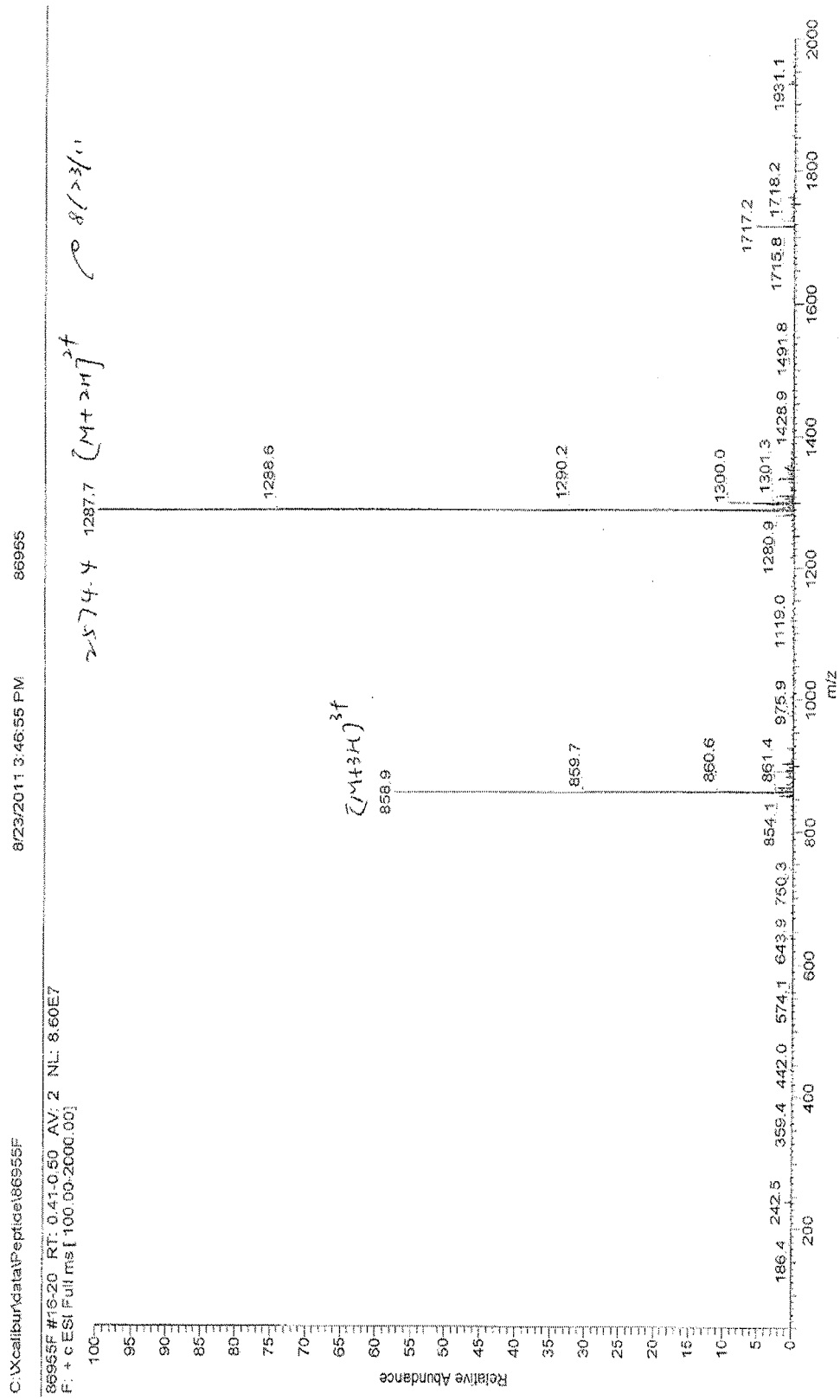
FIG. 5 shows mass spectrometry results for the synthesized HER2 synthetic peptide #2.

Mass spectrometry analysis of samples comprising the synthetic peptides #1 or #2 was performed using a ThermoQuest Finnigan LCQ DUO mass spectrometer. Samples were prepared in 70% water/30% acetonitrile solvent. Electrospray ionization was used to ionize the sample. Isocratic method was used to inject the peptide solution into the ion source of the mass spectrometer. For peptide #1, the theoretical mass ($M+H^+$) was 2983.4, and the mass found ($M+H^+$) was 2982.8, within 1 mass unit of theoretical (FIG. 4). For peptide #2, the theoretical mass ($M+H^+$) was 2575.2, and the mass found ($M+H^+$) was 2574.4, also within 1 mass unit of theoretical (FIG. 5).

Example 3. Generation of Monoclonal Antibodies Against HER2Δ16 Peptides

This example illustrates the methods of the present invention for producing monoclonal antibodies that recognize HER2Δ16 polypeptides. These antibodies can be used for diagnosing the HER2Δ16 or as a therapeutic agent in patients.

Monoclonal anti-HER2Δ16 peptide antibodies are produced by immunizing BALB/c mice with a series of intraperitoneal injections. The initial injection consists of a 1:1 ratio of synthesized HER2Δ16 cyclic peptide in complete Freund's adjuvant. Booster injections of the same amount of antigen in incomplete Freund's adjuvant are given at weekly intervals until the titer is sufficient (usually after three immunizations). A final booster injection of peptide without Freund's adjuvant is given prior to cellular fusion. Mouse spleen cells are harvested and fused with mouse myeloma cells of the line X63-Ag8.653 at a ratio of 6:1 using standard hybridoma production protocols as described in Harlow E. and Lane D. *Antibodies, A Laboratory Manual.* Cold Spring Harbor, N.Y.: Cold Spring Harbor Laboratory Press (1988). After 7-14 days of culturing the fused cells, culture supernatant from hybridoma clones are tested for reactivity to HER2Δ16 peptide using an enzyme-linked immunoassay (ELISA). Positive hybridoma clones are subcloned by limiting cell dilution, then re-tested for reactivity to HER2Δ16 peptide, in order to establish single-cell clones. Positive hybridoma cultures of single-cell clones are then grown in stirred flasks to produce large quantities of monoclonal anti-HER2Δ16 peptide antibodies in vitro.

Monoclonal antibodies are further purified by passing the hybridoma supernatant through a column of synthesized HER2Δ16 peptide linked to a Sepharose 4B9. IgG molecules bound to the peptide are eluted with 0.1M glycine at pH 2.4, and then dialyzed against a buffer composed of 0.02M Tris and 0.15M NaCl adjusted to pH 7.35. The monoclonal antibody can also be concentrated. The mouse monoclonal antibody can be cloned and sequenced using standard recombinant DNA and molecular biology techniques known to those skilled in the art. See, e.g., Sambrook J. and Russell, D. *Molecular Cloning: A Laboratory Manual, Third Edition.* Cold Spring Harbor, N.Y.: Cold Spring Harbor Laboratory Press (2001); Ausubel F M, Brent R, Kingston R E, Moore D D, Seidman J G, Smith J A, Struhl K. *Current Protocols in Molecular Biology.* New York: Wiley (2010).

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated antibody, or antigen-binding fragment thereof, that specifically binds to a HER2Δ16 cyclic peptide having the formula:

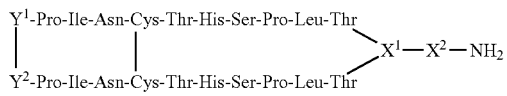

wherein each of $X^1$ and $X^2$ independently is selected from the group consisting of lysine, ornithine, β-amino-alanine, α,γ-diamino-butyric acid, and 2,7-diamino-heptanoic acid;

wherein each of $Y^1$ and $Y^2$ comprises a disulfide bond-forming compound, and wherein $Y^1$ is linked with $Y^2$ via a disulfide bond;

wherein the cysteine residues are linked via a disulfide bond; and wherein $X^1$ and Thr are linked via a peptide bond.

2. The antibody of claim 1, wherein each of $X^1$ and $X^2$ is a lysine.

3. The antibody of claim 1, wherein each of $Y^1$ and $Y^2$ independently is selected from a cysteine residue or beta-mercaptopropionic acid.

4. The antibody of claim 1, wherein the HER2Δ16 cyclic peptide has the structure:

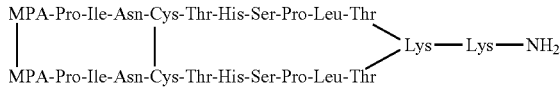

wherein MPA is beta-mercaptopropionic acid.

5. The antibody of claim 1, wherein the antibody is a polyclonal antibody.

6. The antibody of claim 1, wherein the antibody is a monoclonal antibody.

7. The antibody of claim 1, wherein the antibody is a chimeric antibody.

8. The antibody of claim 1, wherein the antibody is a humanized antibody.

9. The antibody of claim 1, wherein the antigen-binding fragment is a Fab, a F(ab')$_2$, or a scFv.

10. The antibody of claim 1, wherein the antibody is conjugated to a label.

11. The antibody of claim 10, wherein the label is a fluorescent label or a radioactive label.

12. The antibody of claim 1, wherein the antibody is conjugated to a therapeutic moiety.

13. The antibody of claim 12, wherein the therapeutic moiety is an anti-cancer drug, a toxin, or a cytokine.

14. A pharmaceutical composition comprising the antibody of claim 1 and a pharmaceutically acceptable carrier.

15. A method of diagnosing a subject having a cancer that expresses HER2Δ16, the method comprising:

contacting a sample from the subject with an antibody that specifically binds to a a HER2Δ16 cyclic peptide having the formula:

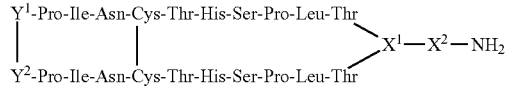

wherein each of $X^1$ and $X^2$ independently is selected from the group consisting of lysine, ornithine, β-amino-alanine, α,γ-diamino-butyric acid, and 2,7-diamino-heptanoic acid; each of $Y^1$ and $Y^2$ comprises a disulfide bond-forming compound, and wherein $Y^1$ is linked with $Y^2$ via a disulfide bond; the cysteine residues are linked via a disulfide bond; and $X^1$ and Thr are linked via a peptide bond; and detecting expression of HER2Δ16 in the sample; thereby diagnosing the subject as having a cancer that expresses HER2Δ16.

16. The method of claim 15, wherein the sample is a tumor tissue sample.

17. The method of claim 15, wherein the cancer is breast cancer.

18. The method of claim 15, wherein the detecting step is performed using an enzyme immunoassay, a radioimmunoassay, or an immunohistochemical assay.

19. The method of claim 18, wherein the detecting step is performed using an ELISA assay.

20. The method of claim 15, wherein the method comprises determining the level of expression of HER2Δ16 in the sample.

* * * * *